United States Patent
Sheng et al.

(10) Patent No.: US 11,111,248 B2
(45) Date of Patent: Sep. 7, 2021

(54) CRYSTAL FORM OF 2-(6-METHYL- PYR-IDIN-2-YL)-3-YL-[6-AMIDO-QUINOLIN-4-YL]-5,6-DIHYDRO-4H-PYRROLO[1,2-B]P-YRAZOLE, PREPARATION METHOD THEREFOR AND PHARMACEUTICAL COMPOSITION THEREOF

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN); Jing Wang, Zhejiang (CN)

(73) Assignee: Hangzhou SoliPharma Co., Ltd., Zhejiang (CN)

( * ) Notice: Subject to any disclaimer, the term of this patent is extended or adjusted under 35 U.S.C. 154(b) by 0 days.

(21) Appl. No.: 16/495,037

(22) PCT Filed: Mar. 17, 2017

(86) PCT No.: PCT/CN2017/077081
§ 371 (c)(1),
(2) Date: Sep. 17, 2019

(87) PCT Pub. No.: WO2018/165979
PCT Pub. Date: Sep. 20, 2018

(65) Prior Publication Data
US 2020/0399272 A1    Dec. 24, 2020

(51) Int. Cl.
*A61K 31/47* (2006.01)
*C07D 215/48* (2006.01)
*C07D 487/04* (2006.01)

(52) U.S. Cl.
CPC ........ *C07D 487/04* (2013.01); *C07B 2200/13* (2013.01)

(58) Field of Classification Search
CPC .............................. A61K 31/47; C07D 215/48
USPC .......................................... 514/314; 546/169
See application file for complete search history.

(56) References Cited

U.S. PATENT DOCUMENTS

| 7,834,029 B2 | 11/2010 | Beight |
| 7,872,020 B2 | 1/2011 | Mundla |
| 10,604,528 B2 | 3/2020 | Chen et al. |
| 2013/0028978 A1 | 1/2013 | Mao |

FOREIGN PATENT DOCUMENTS

| CN | 1714090 A | 12/2005 |
| CN | 102711799 A | 10/2012 |
| WO | WO-2018165979 A1 | 9/2018 |

OTHER PUBLICATIONS

Niemeier, J.K., et al., "Application of Kinetic Modeling and Competitive Solvent Hydrolysis in the Development of a Highly Selective Hydrolysis of a Nitrile to an Amide," Organic Process Research & Development 18(3):410-416, American Chemical Society, United States (2014).

Jin, C., et al., "Synthesis and Biological Evaluation of 1-Substituted-3 (5)-(6-Methylpyridin-2yl)-4-(Quinolin-6-yl) Pyrazoles as Transforming Growth Factor-β Type I Receptor Kinase Inhibitors," Bioorganic & Medicinal Chemistry 19(8):2633-2640, Elsevier, Netherlands (2011).

International Search Report and Written Opinion for International Application No. PCT/CN2017/077081, State Intellectual Property Office of the P.R. China, dated Dec. 22, 2017, 15 pages.

*Primary Examiner* — Douglas M Willis
(74) *Attorney, Agent, or Firm* — Sterne, Kessler, Goldstein & Fox P.L.L.C.

(57) ABSTRACT

The present invention relates to a crystal form of 2-(6-methyl-pyridin-2-yl)-3-(6-amido-quinolin-4-yl)-5,6-dihydro-4h-pyrrolo[1,2-b]pyrazole (Galunisertib or LY2157299), represented by formula (I). Compared with the known solid form of Galunisertib, the crystal form of the present invention has advantages in terms of solubility, hygroscopicity, crystal stability, morphology and the like. The present invention also relates to a process of preparing the crystal forms of Galunisertib, a pharmaceutical composition thereof and a use thereof in the preparation of a medicament for the prevention and/or treatment of diseases associated with TGF-beta.

(I)

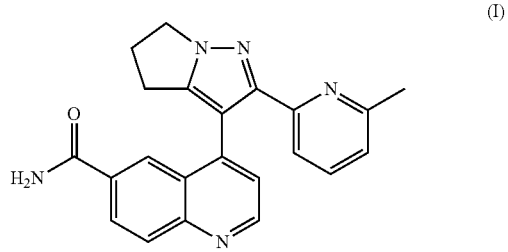

20 Claims, 21 Drawing Sheets

CRYSTAL FORM OF 2-(6-METHYL-PYRIDIN-2-YL)-3-YL-[6-AMIDO-QUINOLIN-4-YL]-5,6-DIHYDRO-4H-PYRROLO[1,2-B]PYRAZOLE, PREPARATION METHOD THEREFOR AND PHARMACEUTICAL COMPOSITION THEREOF

FIELD OF THE INVENTION

The present invention relates to the technical field of crystallization in pharmaceutical chemistry. Specifically, the present invention relates to 2-(6-methyl-pyridin-2-yl)-3-(6-amido-quinolin-4-yl)-5,6-dihydro-4h-pyrrolo[1,2-b]pyrazole crystalline forms thereof, and their preparation methods, pharmaceutical compositions and uses.

BACKGROUND 2-(6-methyl-pyridin-2-yl)-3-(6-amido-quinolin-4-yl)-5,6-dihydro-4h-pyrrolo[1,2-b]pyrazole, another name LY215-7299, is a transforming growth factor-beta (TGF-β) signaling inhibitor, English name Galunisertib. Its chemical structural formula is as following formula (I).

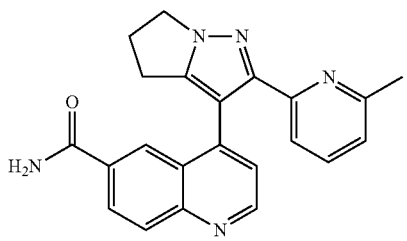

TGF-β includes three subtypes, TGF-β1, TGF-β2 and TGF-β3. It can affect the growth, differentiation and gene expression in many kinds of cells. TGF-β has close relationship with many diseases. As a singling inhibitor of TGF-β, LY2157299 can be used to treat cancers, precancers, kidney diseases, fibrosis, and eye diseases. Patent CN100345852C disclosed LY2157299's preparation methods and mass data; U.S. Pat. No. 7,872,020B2 disclosed LY2157299 monohydrate's preparation method and its HNMR, mass data and XRPD data. The LY2157299 monohydrate described in U.S. Pat. No. 7,872,020B2 has disadvantages in low solubility and thermal phase stability issues.

In view of the disadvantages in the prior art, it is still necessary to develop new solid forms of LY2157299 in this field in order to meet the need in formulation in API solubility, stability and morphology.

SUMMARY OF THE INVENTION

In view of the disadvantages in the prior art, an objective of the present invention is to provide crystalline forms of LY2157299, their preparation methods, uses and pharmaceutical compositions thereof. The said crystalline forms in the present invention should have one or more advantageous properties, especially in crystallinity, solubility, hygrscopicity, morphology, processibility and phase stability.

According to the purpose of the present invention, one aspect of the present invention is to provide Form 1 of 2-(6-methyl-pyridin-2-yl)-3-(6-amido-quinolin-4-yl)-5,6-dihydro-4h-pyrrolo[1,2-b]pyrazole and its preparation methods.

The X-ray powder diffraction pattern of 2-(6-methyl-pyridin-2-yl)-3-(6-amido-quinolin-4-yl)-5,6-dihydro-4h-pyrrolo[1,2-b]pyrazole Form 1, expressed as 2θ angles, has the following characteristic peaks: 10.2°±0.2°, 14.6°±0.2°, 15.8°±0.2°, 19.0°±0.2°, 19.4°±0.2° and 21.9°±0.2°.

In one preferred embodiment, the X-ray powder diffraction pattern of the said Form 1, expressed as 2θ angles, has the following characteristic peaks: 10.2°±0.2°, 11.2°±0.2°, 12.4°±0.2°, 14.6°±0.2°, 15.8°±0.2°, 16.8°±0.2°, 19.0°±0.2°, 19.4°±0.2°, 19.8°±0.2°, 21.9°±0.2°, 23.2°±0.2° and 25.1°±0.2°.

In a further preferred embodiment, the X-ray powder diffraction pattern of the said Form 1, expressed as 2θ angles, has the following characteristic peaks with their relative intensities:

| 2θ | Relative Intensity (%) |
|---|---|
| 9.3° ± 0.2° | 20.2 |
| 10.2° ± 0.2° | 84.6 |
| 11.2° ± 0.2° | 28.3 |
| 12.4° ± 0.2° | 26.3 |
| 13.9° ± 0.2° | 18.9 |
| 14.6° ± 0.2° | 37.7 |
| 15.8° ± 0.2° | 57.4 |
| 16.8° ± 0.2° | 28.3 |
| 17.8° ± 0.2° | 13.8 |
| 19.0° ± 0.2° | 80.6 |
| 19.4° ± 0.2° | 49.4 |
| 19.8° ± 0.2° | 27.4 |
| 20.9° ± 0.2° | 19.4 |
| 21.9° ± 0.2° | 100.0 |
| 22.2° ± 0.2° | 28.2 |
| 23.2° ± 0.2° | 42.2 |
| 23.4° ± 0.2° | 33.3 |
| 25.1° ± 0.2° | 67.1 |
| 25.5° ± 0.2° | 19.3 |

Non-restrictively, in one typical embodiment of the present invention, the X-ray powder diffraction pattern of the said Form 1 is shown in FIG. 6.

Non-restrictively, a DSC thermogram of the said Form 1 is shown in FIG. 7 and has a melting point of 247° C.

Non-restrictively, a TGA thermogram of the said Form 1 is shown in FIG. 8; it is anhydrous and has decomposition temperature of 322° C.

Non-restrictively, an isothermal sorption curve of the said Form 1 is shown in FIG. 8 and has a weight change of 0.19%, less than 0.2% and non-hygroscopic.

Compared with the known LY2157299 monohydrate, the Form 1 of the present invention has the following beneficial properties:

(1) The Form 1 of the present invention has a water solubility of about 160 ug/mL, while the known LY2157299 monohydrate has a water solubility less than 50 ug/mL, therefore the Form 1 of present invention has better water solubility.

(2) From DSC and TGA thermograms, the known LY2157299 monohydrate dehydrates under temperature and its phase transformes, while the Form 1 of the present invention has no phase transformation before melting, therefore Form 1 has better phase stability.

(3) From isothermal sorption curve, the known LY2157299 monohydrate has a weight change greater than 0.2% from 0% RH to 80% RH while the Form 1 of the present invention has a weight change less than 0.2% from 0% RH to 80% RH, therefore less hygroscopic.

(4) As compared with the known LY2157299 monohydrate, the Form 1 of the present invention is anhydrous and has higher content at the same mass level.

The above advantageous properties of the Form 1 of the present invention show that, compared with the known LY2157299 monohydrate, the Form 1 of the present invention has many advantages and is more suitable for being used as the solid form of the active ingredient in pharmaceutical formulations. The known LY2157299 monohydrate has low water solubility and worse thermal phase stability, which can affect the quality and stability of formulation. The Form 1 of the present invention has higher solubility, therefore higher dissolution rate and better bioavailability. Form 1 also has lower hygroscopicity and better phase stability which can better ensure the quality of the active ingredients and formulations containing LY2157299, avoiding and reducing quality issues, safety issues and stability issues during pharmaceutical production and/or storage, such as content uniformity and impurity issues, avoiding special and expensive package.

The present invention provides preparation methods of Form 1, which include any one of the following methods:

(1) forming a solution of LY2157299 in a co-solvent, dropwisely adding the solution to an anti-solvent, stirring for crystallization, separating crystals and drying to obtain the said Form 1;

preferably, the co-solvent is a $C_3$ to $C_4$ ketone, more preferably acetone;

preferably, the weight to volume ratio of LY2157299 to the co-solvent is from 5 mg:1 mL to 40 mg:1 mL, more preferably from 5 mg:1 mL to 20 mg:1 mL;

preferably, the anti-solvent is selected from the group consisting of a $C_4$ to $C_6$ ether, n-heptane, and any mixture thereof, more preferably diisopropyl ether;

preferably, the stirring time is 0.5 to 2 hours;

preferably, the stirring is at 0° C. to 5° C.;

2) heating LY2157299 monohydrate, and then cooling to room temperature to obtained the said Form 1;

preferably, the said heating is up to 130° C. to 180° C.;

preferably, the said heating is at a rate of 1° C./min to 50° C./min, more preferably 1° C./min to 10° C./min;

preferably, the said cooling is at a rate of 1° C./min to 50° C./min, more preferably 1° C./min to 10° C./min.

According to the purpose of the present invention, the second aspect of the present invention is to provide Form 2 of 2-(6-methyl-pyridin-2-yl)-3-(6-amido-quinolin-4-yl)-5,6-dihydro-4h-pyrrolo[1,2-b]pyrazole and its preparation methods.

The X-ray powder diffraction pattern of 2-(6-methyl-pyridin-2-yl)-3-(6-amido-quinolin-4-yl)-5,6-dihydro-4h-pyrrolo[1,2-b]pyrazole Form 2, expressed as 2θ angles, has the following characteristic peaks: 7.9°±0.2°, 11.7°±0.2°, 12.9°±0.2°, 14.7°±0.2°, 20.5°±0.2° and 21.9°±0.2°.

In one preferred embodiment, the X-ray powder diffraction pattern of 2-(6-methyl-pyridin-2-yl)-3-(6-amido-quinolin-4-yl)-5,6-dihydro-4h-pyrrolo[1,2-b]pyrazole Form 2, expressed as 2θ angles, has the following characteristic peaks: 7.9°±0.2°, 11.7°±0.2°, 12.2°±0.2°, 12.9°±0.2°, 14.7°±0.2°, 15.4°±0.2°, 16.0°±0.2°, 18.5°±0.2°, 20.5°±0.2°, 21.9°±0.2°, 22.3°±0.2° and 25.6°±0.2°.

In a further preferred embodiment, the X-ray powder diffraction pattern of the said Form 2, expressed as 2θ angles, has the following characteristic peaks with their relative intensities:

| 2θ | Relative Intensity (%) |
| --- | --- |
| 7.9° ± 0.2° | 100.0 |
| 11.7° ± 0.2° | 23.5 |
| 12.2° ± 0.2° | 12.7 |
| 12.9° ± 0.2° | 23.6 |
| 14.7° ± 0.2° | 15.0 |
| 15.4° ± 0.2° | 16.1 |
| 16.0° ± 0.2° | 14.3 |
| 16.5° ± 0.2° | 3.7 |
| 17.0° ± 0.2° | 3.4 |
| 18.5° ± 0.2° | 12.1 |
| 19.0° ± 0.2° | 3.2 |
| 19.3° ± 0.2° | 2.6 |
| 20.1° ± 0.2° | 3.6 |
| 20.5° ± 0.2° | 27.4 |
| 21.9° ± 0.2° | 39.8 |
| 22.3° ± 0.2° | 9.9 |
| 23.2° ± 0.2° | 3.0 |
| 24.1° ± 0.2° | 9.3 |
| 25.6° ± 0.2° | 20.0 |
| 26.7° ± 0.2° | 7.7 |
| 29.8° ± 0.2° | 5.0 |

Non-restrictively, in one typical embodiment of the present invention, the X-ray powder diffraction pattern of the said Form 2 is shown in FIG. 10.

Non-restrictively, a DSC thermogram of the said Form 2 is shown in FIG. 11 and has a melting point of 248° C.

Non-restrictively, a TGA thermogram of the said Form 2 is shown in FIG. 12; it is anhydrous and has decomposition temperature of 322° C.

Non-restrictively, an isothermal sorption curve of the said Form 2 is shown in FIG. 13 and has a weight change of 0.25%, slightly hygroscopic.

Compared with the known LY2157299 monohydrate, the Form 2 of the present invention has the following beneficial properties:

(1) The Form 2 of the present invention has a water solibility of about 200 ug/mL, while the known LY2157299 monohydrate has a water solubility less than 50 ug/mL, therefore the Form 1 of present invention has better water solubility.

(2) From DSC thermograms, the known LY2157299 monohydrate dehydrates under temperature and has a phase transition temperature 60° C. lower than that of the Form 2 of the present invention, therefore Form 2 has a higher phase transition temperature and better phase stability.

(3) As compared with the known LY2157299 monohydrate, the Form 2 of the present invention is anhydrous and has higher content at the same mass.

The above advantageous properties of the Form 2 of the present invention show that, compared with the known LY2157299 monohydrate, the Form 2 of the present invention has many advantages and is more suitable for being used as the solid form of the active ingredient in pharmaceutical formulations. The known LY2157299 monohydrate has low water solubility and bad thermal phase stability, which can affect the quality and stability of formulation. The Form 2 of the present invention has higher solubility, therefore higher dissolution rate and better bioavailability. In addition Form 2 has better phase stability which can better ensure the quality of the active ingredients and formulations containing LY2157299, avoiding and reducing quality issues, safety issues and stability issues during pharmaceutical production and/or storage, such as content uniformity and impurity issues, avoiding special and expensive package.

The present invention provides preparation methods of Form 2, which include any one of the following:

(1) forming a solution of LY2157299 in a solvent, evaporating to dryness to obtain the said Form 2;

preferably, the solvent is selected from the group consisting of tetrahydrofuran (THF), isopropanol, n-propanol, isopropyl acetate, and any mixture thereof, more preferably isopropanol;

preferably, the weight to volume ratio of LY2157299 to the solvent is from 2.5 mg:1 mL to 12.5 mg:1 mL;

preferably, the evaporation is at 25° C. to 40° C.;

preferably, the evaporation is atmospheric evaporation or reduced-pressure evaporation, more preferably atmospheric pressure evaporation;

(2) forming a suspension of Form 1 of the present invention in a solvent, stirring for crystallization, separating crystals and drying to obtain the said Form 2;

preferably, the solvent is tetrahydrofuran or a mixture of isopropyl acetate and toluene;

preferably, the weight to volume ratio of the said Form 1 to the solvent is from 10 mg:1 mL to 100 mg:1 mL, more preferably from 50 mg:1 mL to 100 mg:1 mL; preferably, the stirring is for 3 to 7 days;

preferably, the stirring is under 25° C.-60° C.;

(3) forming a solution of LY2157299 in tetrahydrofuran, stirring and cooling for crystallization, separating crystals and drying to obtain the said Form 2;

preferably, the solution is formed at 50° C. to 55° C.;

preferably, the weight to volume ratio of LY2157299 to tetrahydrofuran is from 20 mg:1 mL to 30 mg:1 mL;

preferably, the stirring is at 0° C. to 25° C., more preferably, the stirring is at 0° C. to 5° C.;

preferably, the stirring time is 0.5 to 5 hours.

According to the purpose of the present invention, the third aspect of the present invention is to provide Form 3 of 2-(6-methyl-pyridin-2-yl)-3-(6-amido-quinolin-4-yl)-5,6-dihydro-4h-pyrrolo[1,2-b]pyrazole and its preparation methods.

The X-ray powder diffraction pattern of 2-(6-methyl-pyridin-2-yl)-3-(6-amido-quinolin-4-yl)-5,6-dihydro-4h-pyrrolo[1,2-b]pyrazole Form 3, expressed as 2θ angles, has the following characteristic peaks: 8.6°±0.2°, 12.3°±0.2°, 14.5°±0.2°, 17.9°±0.2°, 19.4°±0.2° and 21.0°±0.2°.

In one preferred embodiment, the X-ray powder diffraction pattern of LY2157299 Form 2, expressed as 2θ angles, has the following characteristic peaks: 8.6°±0.2°, 10.0°±0.2°, 11.9°±0.2°, 12.3°±0.2°, 14.5°±0.2°, 15.6°±0.2°, 17.3°±0.2°, 17.9°±0.2°, 19.4°±0.2°, 20.4°±0.2°, 21.0°±0.2° and 21.9°±0.2°.

In a further preferred embodiment, the X-ray powder diffraction pattern of the said Form 3, expressed as 2θ angles, has the following characteristic peaks with their relative intensities:

| 2θ | Relative Intensity (%) |
|---|---|
| 8.6° ± 0.2° | 18.7 |
| 10.0° ± 0.2° | 39.0 |
| 11.9° ± 0.2° | 33.5 |
| 12.3° ± 0.2° | 57.0 |
| 13.7° ± 0.2° | 31.3 |
| 14.5° ± 0.2° | 100.0 |
| 15.4° ± 0.2° | 28.5 |
| 15.6° ± 0.2° | 41.6 |
| 17.3° ± 0.2° | 31.5 |
| 17.9° ± 0.2° | 57.2 |
| 19.4° ± 0.2° | 44.4 |

-continued

| 2θ | Relative Intensity (%) |
|---|---|
| 19.6° ± 0.2° | 29.4 |
| 20.4° ± 0.2° | 43.8 |
| 21.0° ± 0.2° | 49.0 |
| 21.9° ± 0.2° | 36.0 |
| 22.5° ± 0.2° | 20.8 |
| 23.5° ± 0.2° | 20.2 |
| 24.0° ± 0.2° | 22.9 |
| 24.9° ± 0.2° | 37.7 |
| 25.7° ± 0.2° | 31.4 |
| 31.3° ± 0.2° | 15.9 |

Non-restrictively, in one typical embodiment of the present invention, the X-ray powder diffraction pattern of the said Form 3 is shown in FIG. 14.

Non-restrictively, a DSC thermogram of the said Form 3 is shown in FIG. 15 and has a melting point of 241° C.

Non-restrictively, a TGA thermogram of the said Form 3 is shown in FIG. 16; it is anhydrous and has decomposition temperature of 321° C.

Non-restrictively, an isothermal sorption curve of the said Form 3 is shown in FIG. 17 and has a weight change of 0.19%, less than 0.2%, non-hygroscopic.

Compared with the known LY2157299 monohydrate, the Form 3 of the present invention has the following beneficial properties:

(1) The Form 3 of the present invention has a water solubility of about 150 μg/mL, while the known LY2157299 monohydrate has water solubility less than 50 μg/mL, therefore the Form 3 of present invention has better water solubility.

(2) From DSC and TGA thermograms, the known LY2157299 monohydrate dehydrates under temperature and has phase transformation, while the Form 3 of the present invention has no phase transformation before melting; therefore Form 1 has better phase stability.

(3) From isothermal sorption curve, the known LY2157299 monohydrate has a weight change greater than 0.2% from 0% RH to 80% RH while the Form 3 of the present invention has a weight change less than 0.2% from 0% RH to 80% RH, therefore less hygroscopic.

As compared with the known LY2157299 monohydrate, the Form 3 of the present invention is anhydrous and has higher content at the same mass.

The above advantageous properties of the Form 3 of the present invention show that, compared with the known LY2157299 monohydrate, the Form 3 of the present invention has many advantages and is more suitable for being used as the solid form of the active ingredient in pharmaceutical formulations. The known LY2157299 monohydrate has low water solubility and worse thermal phase stability, which can affect the quality and stability of formulation. The Form 3 of the present invention has higher solubility, therefore higher dissolution rate and better bioavailability, Form 3 also has lower hygroscopicity and better phase stability which can better ensure the quality of the active ingredients and formulations containing LY2157299, avoiding and reducing quality issues, safety issues and stability issues during pharmaceutical production and/or storage, such as content uniformity and impurity issues, avoiding special and expensive package. The present invention provides preparation methods of Form 3, which include any one of the following:

(1) forming a solution of LY2157299 in acetonitrile, evaporating to dryness to obtain the said Form 3;

preferably, the weight to volume ratio of LY2157299 to solvent is from 2.5 mg:1 mL to 20 mg:1 mL, more preferably 10 mg:1 mL to 20 mg:1 mL;

preferably, the evaporation is reduced-pressure evaporation, at 30° C. to 40° C.;

(2) forming a suspension of Form 1 of the present invention in a solvent, stir for crystallization, separating crystals and drying to obtain the said Form 3;

preferably, the solvent is selected from the group consisting of a $C_3$ to $C_4$ ester, acetonitrile, a $C_3$ to $C_4$ ketone, a $C_4$ to $C_6$ ether, and any mixture thereof, more preferably ethyl acetate, acetonitrile, acetone, methyl tert-butyl ether or their mixture;

preferably, the weight to volume ratio of Form 1 of the present invention to the solvent is from 10 mg:1 mL to 100 mg:1 mL, more preferably 50 mg:1 mL to 100 mg:1 mL;

preferably, the stirring time is 3 to 7 days;

more preferably, the stirring is at 4° C. to 40° C.;

(3) forming a solution of LY2157299 in a solvent, stirring and cooling for crystallization, separating crystals and drying to obtain the said Form 3;

preferably, the solvent is selected from the group consisting acetonitrile, a mixture of acetonitrile and ethyl acetate, and a mixture of acetonitrile and methyl tert-butyl ether;

preferably, the solution is formed at 50° C. to 60° C.;

preferably, the weight to volume ratio of LY2157299 to solvent is from 10 mg:1 mL to 50 mg:1 mL, more preferably 10 mg:1 mL to 20 mg:1 mL;

preferably, the stirring is at 0° C. to 5° C.;

preferably, the stirring is for 1 to 3 hr;

(4) forming a solution of LY2157299 in a co-solvent, adding an anti-solvent, stirring for crystallization, separating crystals and drying to obtain the said Form 3;

preferably, the co-solvent is acetonitrile or ethyl acetate;

preferably, the weight to volume ratio of LY2157299 to the co-solvent is from 5 mg:1 mL to 20 mg:1 mL;

preferably, the anti-solvent is a $C_4$ to $C_6$ ether, more preferably diisopropyl ether; preferably, the stirring time is 0.5 to 2 hours;

preferably, the stirring time is at 0° C. to 5° C.

According to the purpose of the present invention, the fourth aspect of the present invention is to provide Form 4 of 2-(6-methyl-pyridin-2-yl)-3-(6-amido-quinolin-4-yl)-5,6-dihydro-4h-pyrrolo[1,2-b]pyrazole and its preparation methods.

The X-ray powder diffraction pattern of 2-(6-methyl-pyridin-2-yl)-3-(6-amido-quinolin-4-yl)-5,6-dihydro-4h-pyrrolo[1,2-b]pyrazole Form 4, expressed as 2θ angles, has the following characteristic peaks: 5.9°±0.2°, 11.7°±0.2°, 12.2°±0.2°, 14.1°±0.2°, 16.4°±0.2° and 21.8°±0.2°.

In one preferred embodiment, the X-ray powder diffraction pattern of 2-(6-methyl-pyridin-2-yl)-3-(6-amido-quinolin-4-yl)-5,6-dihydro-4h-pyrrolo[1,2-b]pyrazole Form 4, expressed as 2θ angles, has the following characteristic peaks: 5.9°±0.2°, 11.7°±0.2°, 12.2°±0.2°, 13.5°±0.2°, 14.1°±0.2°, 16.4°±0.2°, 17.4°±0.2°, 18.2°±0.2°, 20.0°±0.2°, 21.8°±0.2°, 22.4°±0.2° and 26.1°±0.2°.

In a further preferred embodiment, the X-ray powder diffraction pattern of the said Form 4, expressed as 2θ angles, has the following characteristic peaks with their relative intensities:

| 2θ | Relative Intensity (%) |
| --- | --- |
| 5.9° ± 0.2° | 100.0 |
| 11.7° ± 0.2° | 20.8 |
| 12.2° ± 0.2° | 58.9 |
| 13.5° ± 0.2° | 17.3 |
| 14.1° ± 0.2° | 18.0 |
| 16.4° ± 0.2° | 21.0 |
| 17.4° ± 0.2° | 15.7 |
| 18.2° ± 0.2° | 10.0 |
| 18.8° ± 0.2° | 9.7 |
| 20.0° ± 0.2° | 31.3 |
| 21.8° ± 0.2° | 52.1 |
| 22.4° ± 0.2° | 23.7 |
| 22.9° ± 0.2° | 8.1 |
| 26.1° ± 0.2° | 21.9 |

Non-restrictively, in one typical embodiment of the present invention, the X-ray powder diffraction pattern of the said Form 4 is shown in FIG. 18.

Non-restrictively, a DSC thermogram of the said Form 4 is shown in FIG. 19. It desolvates at 100° C. to 150° C., melts and phase transfers at 215° C., then melts at 240° C. and 247° C.

Non-restrictively, a TGA thermogram of the said Form 4 is shown in FIG. 20; it is anhydrous and has decomposition temperature of 325° C.

Non-restrictively, an isothermal sorption curve of the said Form 4 is shown in FIG. 21 and has a weight change of 0.95% and slightly hygroscopic.

Non-restrictively, a PLM plot of the said Form 4 is shown in FIG. 22 and shows regular block-like crystals.

Compared with the known LY2157299 monohydrate, the Form 4 of the present invention has the following beneficial properties:

(1) The Form 4 of the present invention has a water solubility of about 100 ug/mL, while the known LY2157299 monohydrate has a water solubility less than 50 ug/mL, therefore the Form 4 of present invention has better water solubility.

(2) The Form 4 of the present invention has regular block-like crystals, while the known LY2157299 monohydrate is needle like, therefore the Form 4 of present invention has better processibility.

(3) As compared with the known LY2157299 monohydrate, the Form 4 of the present invention is anhydrous and has higher active content at the same mass.

The above advantageous properties of the Form 4 of the present invention show that, compared with the known LY2157299 monohydrate, the Form 4 of the present invention has many advantages and is more suitable for being used as the solid form of the active ingredient in pharmaceutical formulations. The known LY2157299 monohydrate has low water solubility and bad thermal phase stability, which can affect the quality and stability of formulation. The Form 4 of the present invention has higher solubility, therefore higher dissolution rate and better bioavailability. The known LY2157299 monohydrate is needle-like, therefore has bad flowability and processibility while the Form 4 of the present invention has regular block-like crystals therefore has better flowability and processibility.

The present invention provides preparation methods of Form 4, which include any one of the following:

(1) forming a suspension of Form 1 of the present invention in a solvent, stirring for crystallization, separating crystals and drying to obtain the said Form 4;

preferably, the solvent is selected from the group consisting methanol, a mixture of methanol and ethyl acetate, and a mixture of ethanol and n-heptane;

preferably, the weight to volume ratio of the said Form 1 to the solvent is from 10 mg:1 mL to 100 mg:1 mL, more preferably from 12.5 mg:1 mL to 50 mg:1 mL;

preferably, the stirring is for 3 to 7 days;

preferably, the stirring is under 4° C. to 60° C., more preferably 4° C. to 25° C.;

(2) forming a solution of LY2157299 in a solvent, stirring and cooling for crystallization, separating crystals and drying to obtain the said Form 4;

preferably, the solvent is selected from the group consisting of methanol, a mixture of methanol and methyl tert-butyl ether, and a mixture of methanol and isopropyl acetate;

preferably, the solution is formed at 50° C. to 55° C.;

preferably, the weight to volume ratio of LY2157299 to the solvent is from 10 mg:1 mL to 50 mg:1 mL, more preferably 10 mg:1 mL to 30 mg:1 mL;

more preferably, the stirring is at 0° C. to 5° C.;

preferably, the stirring time is 0.5 to 3 hours;

(3) forming a solution of LY2157299 in a co-solvent, adding an anti-solvent, stirring for crystallization, separating crystals and drying to obtain the said Form 4;

preferably, the co-solvent is a $C_1$ to $C_4$ alcohol, more preferably methanol or ethanol;

preferably, the weight to volume ratio of LY2157299 to the co-solvent is from 5 mg:1 mL to 30 mg:1 mL;

preferably, the anti-solvent is diisopropyl ether or n-heptane;

preferably, the stirring time is 0.5 to 2 hours;

preferably, the stirring time is at 0° C. to 5° C.

According to the purpose of the present invention, the fifth aspect of the present invention is to provide Form 7 of 2-(6-methyl-pyridin-2-yl)-3-(6-amido-quinolin-4-yl)-5,6-dihydro-4h-pyrrolo[1,2-b]pyrazole and its preparation methods.

The 2-(6-methyl-pyridin-2-yl)-3-(6-amido-quinolin-4-yl)-5,6-dihydro-4h-pyrrolo[1,2-b]pyrazole Form 7 has 0.5 mole to 1.0 mole of water; preferably the said Form 7 is a hemihydrate, using Cu-Kα radiation, the X-ray powder diffraction pattern of Form 7, expressed as 2θ angles, has the following characteristic peaks: 7.0°±0.2°, 8.6°±0.2°, 14.2°±0.2°, 16.7°±0.2°, 21.4°±0.2° and 23.4°±0.2°.

In one preferred embodiment, the X-ray powder diffraction pattern of LY2157299 Form 7, expressed as 2θ angles, has the following characteristic peaks: 7.0°±0.2°, 8.6°±0.2°, 12.1°±0.2°, 14.2°±0.2°, 16.4°±0.2°, 16.7°±0.2°, 18.1°±0.2°, 21.0°±0.2°, 21.4°±0.2°, 22.4°±0.2°, 23.4°±0.2° and 25.5°±0.2°.

In a further preferred embodiment, the X-ray powder diffraction pattern of the said Form 7, expressed as 2θ angles, has the following characteristic peaks with their relative intensities:

| 2θ | Relative intensity (%) |
| --- | --- |
| 7.0° ± 0.2° | 17.1 |
| 8.6° ± 0.2° | 8.5 |
| 12.1° ± 0.2° | 5.7 |
| 12.7° ± 0.2° | 4.0 |
| 14.2° ± 0.2° | 100.0 |
| 16.4° ± 0.2° | 7.3 |
| 16.7° ± 0.2° | 11.2 |
| 18.1° ± 0.2° | 5.6 |
| 19.4° ± 0.2° | 4.7 |
| 21.0° ± 0.2° | 8.1 |
| 21.4° ± 0.2° | 18.5 |
| 21.8° ± 0.2° | 4.9 |
| 22.4° ± 0.2° | 5.0 |
| 23.4° ± 0.2° | 16.7 |
| 25.5° ± 0.2° | 7.1 |

Non-restrictively, in one typical embodiment of the present invention, the X-ray powder diffraction pattern of the said Form 7 is shown in FIG. 25.

Non-restrictively, a DSC thermogram of the said Form 7 is shown in FIG. 26. It desolvates before 150° C., melts and phase transfers at 180° C. and then melts at 240° C. and 248° C.

Non-restrictively, a TGA thermogram of the said Form 7 is shown in FIG. 27; it has a weight loss of about 2.9%, about 0.5 mole of water and has a decomposition temperature of 320° C.

Non-restrictively, a PLM plot of the said Form 7 is shown in FIG. 28 and shows regular column-like crystals.

Compared with the known LY2157299 monohydrate, the Form 7 of the present invention has the following beneficial properties:

(1) The Form 7 of the present invention has a water solibility of about 100 μg/mL, while the known LY2157299 monohydrate has water solubility less than 50 μg/mL, therefore the Form 3 of present invention has better water solubility.

(2) The Form 7 of the present invention has regular column-like crystals, while the known LY2157299 monohydrate is needle like, therefore the Form 7 of present invention has better processibility.

(3) As compared with the known LY2157299 monohydrate, the Form 7 of the present invention is hemihydrate and has higher active content at the same mass.

The above advantageous properties of the Form 7 of the present invention show that, compared with the known LY2157299 monohydrate, the Form 7 of the present invention has many advantages and is more suitable for being used as the solid form of the active ingredient in pharmaceutical formulations. The known LY2157299 monohydrate has low water solubility which can affect the quality and stability of formulation. The Form 7 of the present invention has higher solubility, therefore higher dissolution rate and better bioavailability. The known LY2157299 monohydrate is needle-like, therefore has bad flowability and processibility while the Form 7 of the present invention has regular column-like crystals therefore has better flowability and processibility.

The present invention provides preparation methods of Form 7, which include the following:

forming a solution of LY2157299 in water-saturated trichloromethane, evaporating to dryness to obtain LY2157299 Form 7;

preferably, the weight to volume ratio of LY2157299 to the solvent is from 10 mg:1 mL to 25 mg:1 mL;

preferably, the evaporation is atmospheric evaporation or reduced-pressure evaporation;

preferably, the evaporation is at 25° C. to 40° C.

According to the purpose of the present invention, the sixth aspect of the present invention is to provide Form 5 of 2-(6-methyl-pyridin-2-yl)-3-(6-amido-quinolin-4-yl)-5,6-dihydro-4h-pyrrolo[1,2-b]pyrazole and its preparation methods.

The 2-(6-methyl-pyridin-2-yl)-3-(6-amido-quinolin-4-yl)-5,6-dihydro-4h-pyrrolo[1,2-b]pyrazole Form 5 has 0.5 mole to 1 mole of trifluoroethanol. Using Cu-Kα radiation, the X-ray powder diffraction pattern of Form 5, expressed as 2θ angles, has the following characteristic peaks: 7.9°±0.2°, 8.3°±0.2°, 10.7°±0.2°, 11.1°±0.2°, 13.4°±0.2°, 14.0°±0.2°, 16.2°±0.2°, 19.2°±0.2°, 20.3°±0.2°, 21.0°±0.2°, 23.2°±0.2° and 24.3°±0.2°.

Non-restrictively, in one typical embodiment of the present invention, the X-ray powder diffraction pattern of the said Form 5 is shown in FIG. 23.

The present invention provides preparation methods of Form 5, which include any one of the following:

(1) forming a solution of LY2157299 in trifluoroethanol or a mixture of trifluoroethanol and diisopropyl ether, stirring and cooling for crystallization, separating crystals and drying to obtain the said Form 5;

(2) forming a suspension of LY2157299 in trifluoroethanol, adding anti-solvent diisopropyl ether or n-heptane, stirring for crystallization, separating crystals and drying to obtain the said Form 5.

According to the purpose of the present invention, the seventh aspect of the present invention is to provide Form 6 of 2-(6-methyl-pyridin-2-yl)-3-(6-amido-quinolin-4-yl)-5,6-dihydro-4h-pyrrolo[1,2-b]pyrazole and its preparation methods.

The 2-(6-methyl-pyridin-2-yl)-3-(6-amido-quinolin-4-yl)-5,6-dihydro-4h-pyrrolo[1,2-b]pyrazole Form 6 has 0 mole to 0.5 mole of dichloromethane. Using Cu-Kα radiation, the X-ray powder diffraction pattern of Form 6, expressed as 2θ angles, has the following characteristic peaks: 7.0°±0.2°, 8.8°±0.2°, 12.1°±0.2°, 12.6°±0.2°, 14.1°±0.2°, 16.7°±0.2°, 18.2°±0.2°, 19.7°±0.2°, 20.1°±0.2°, 21.3°±0.2°, 23.4°±0.2° and 24.1°±0.2°.

Non-restrictively, in one typical embodiment of the present invention, the X-ray powder diffraction pattern of the said Form 6 is shown in FIG. 24.

The present invention provides a preparation method of Form 6, which include any one of the following:

(1) forming a solution of LY2157299 in dichloromethane, evaporating to dryness to obtain the said Form 6;

(2) forming a solution of LY2157299 in dichloromethane, adding an anti-solvent, stirring for crystallization, separating crystals and drying to obtain the said Form 6.

According to the purpose of the present invention, the eighth aspect of the present invention is to provide Form 8 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 8, expressed as 2θ angles, has the following characteristic peaks: 6.8°±0.2°, 8.1°±0.2°, 10.2°±0.2°, 11.9°±0.2°, 13.8°±0.2°, 16.7°±0.2°, 19.1°±0.2°, 20.2°±0.2°, 20.7°±0.2°, 21.6°±0.2°, 23.0°±0.2° and 25.1°±0.2°.

Non-restrictively, in one typical embodiment of the present invention, the X-ray powder diffraction pattern of the said Form 8 is shown in FIG. 29.

The present invention provides a preparation method of Form 8, which include following steps: Forming a solution of LY2157299 in 2-butanol, evaporating to dryness to obtain the said Form 8;

According to the purpose of the present invention, the ninth aspect of the present invention is to provide Form 9 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 9, expressed as 2θ angles, has the following characteristic peaks: 6.9°±0.2°, 8.6°±0.2°, 12.9°±0.2°, 14.0°±0.2°, 17.0°±0.2°, 20.0°±0.2°, 21.8°±0.2°, 22.5°±0.2°, 23.0°±0.2°, 24.2°±0.2°, 26.1°±0.2° and 26.8°±0.2°.

Non-restrictively, in one typical embodiment of the present invention, the X-ray powder diffraction pattern of the said Form 9 is shown in FIG. 30.

The present invention provides preparation methods of Form 9, which include any one of the following:

(1) forming a suspension of LY2157299 in nitromethane, stirring for crystallization, separating crystals and drying to obtain the said Form 9;

(2) forming a solution of LY2157299 in nitromethane, adding anti-solvent, stirring for crystallization, separating crystals and drying to obtain the said Form 9.

According to the purpose of the present invention, the tenth aspect of the present invention is to provide Form 10 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 10, expressed as 2θ angles, has the following characteristic peaks: 7.1°±0.2°, 10.4°±0.2°, 11.2°±0.2°, 12.4°±0.2°, 12.9°±0.2°, 14.7°±0.2°, 15.9°±0.2°, 19.5°±0.2°, 20.8°±0.2°, 21.8°±0.2°, 22.2°±0.2° and 23.7°±0.2°.

Non-restrictively, in one typical embodiment of the present invention, the X-ray powder diffraction pattern of the said Form 10 is shown in FIG. 31.

The present invention provides preparation methods of Form 10, which include any one of the following:

(1) forming a suspension of LY2157299 in isopropanol, stirring for crystallization, separating crystals and drying to obtain the said Form 10;

(2) forming a solution of LY2157299 in isopropanol, cooling for crystallization, separating crystals and drying to obtain the said Form 10.

According to the purpose of the present invention, the eleventh aspect of the present invention is to provide Form 11 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 11, expressed as 2θ angles, has the following characteristic peaks: 6.9°±0.2°, 11.0°±0.2°, 12.0°±0.2°, 12.9°±0.2°, 15.2°±0.2°, 15.7°±0.2°, 16.6°±0.2°, 19.0°±0.2°, 19.3°±0.2°, 21.8°±0.2°, 22.8°±0.2° and 24.0°±0.2°.

Non-restrictively, in one typical embodiment of the present invention, the X-ray powder diffraction pattern of the said Form 11 is shown in FIG. 32.

The present invention provides preparation methods of Form 11, which include any one of the following:

(1) forming a suspension of LY2157299 in n-propanol, stirring for crystallization, separating crystals and drying to obtain the said Form 11;

(2) forming a solution of LY2157299 in n-propanol, cooling for crystallization to obtain the said Form 11.

According to the purpose of the present invention, the twelfth aspect of the present invention is to provide Form 12 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 12, expressed as 2θ angles, has the following characteristic peaks: 7.0°±0.2°, 12.1°±0.2°, 12.6°±0.2°, 14.8°±0.2°, 15.7°±0.2°, 16.2°±0.2°, 17.9°±0.2°, 19.2°±0.2°, 20.5°±0.2°, 21.2°±0.2°, 22.1°±0.2° and 23.3°±0.2°.

Non-restrictively, in one typical embodiment of the present invention, the X-ray powder diffraction pattern of the said Form 12 is shown in FIG. 33.

The present invention provides a preparation method of Form 12, which include the following steps: forming a suspension of LY2157299 in 2-butanol, stirring for crystallization, separating crystals and drying to obtain the said Form 12.

According to the purpose of the present invention, the thirteenth aspect of the present invention is to provide Form 13 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 13, expressed as 2θ angles, has the following characteristic peaks: 6.9°±0.2°, 10.9°±0.2°, 11.9°±0.2°, 12.5°±0.2°, 14.9°±0.2°, 15.8°±0.2°, 18.4°±0.2°, 19.3°±0.2°, 20.3°±0.2°, 21.5°±0.2°, 22.7°±0.2° and 23.4°±0.2°.

Non-restrictively, in one typical embodiment of the present invention, the X-ray powder diffraction pattern of the said Form 13 is shown in FIG. 34.

The present invention provides a preparation method of Form 13, which include any one of the following:

(1) forming a suspension of LY2157299 in n-butanol, stirring for crystallization, separating crystals and drying to obtain the said Form 13;

(2) forming a solution of LY2157299 in n-butanol, cooling for crystallization to obtain the said Form 13;

(3) forming a solution of LY2157299 in n-butanol, adding an anti-solvent, stirring for crystallization, separating crystals and drying to obtain the said Form 13.

According to the purpose of the present invention, the fourteenth aspect of the present invention is to provide Form 14 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 14, expressed as 2θ angles, has the following characteristic peaks: 6.5°±0.2°, 8.4°±0.2°, 11.7°±0.2°, 12.2°±0.2°, 13.1°±0.2°, 14.9°±0.2°, 16.0°±0.2°, 18.0°±0.2°, 19.5°±0.2°, 20.0°±0.2°, 23.7°±0.2° and 24.7°±0.2°.

Non-restrictively, in one typical embodiment of the present invention, the X-ray powder diffraction pattern of the said Form 14 is shown in FIG. 35.

The present invention provides a preparation method of Form 14, which include the following steps: forming a suspension of LY2157299 in toluene, stirring for crystallization, separating crystals and drying to obtain the said Form 14.

According to the purpose of the present invention, the fifteenth aspect of the present invention is to provide Form 15 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 15, expressed as 2θ angles, has the following characteristic peaks: 6.1°±0.2°, 9.0°±0.2°, 10.0°±0.2°, 12.1°±0.2°, 13.4°±0.2°, 15.8°±0.2°, 17.4°±0.2°, 20.1°±0.2°, 20.7°±0.2°, 21.7°±0.2°, 23.4°±0.2° and 24.5°±0.2°.

Non-restrictively, in one typical embodiment of the present invention, the X-ray powder diffraction pattern of the said Form 15 is shown in FIG. 36.

The present invention provides a preparation method of Form 15, which include any one of the following:

(1) forming a suspension of LY2157299 in ethanol, stirring for crystallization, separating crystals and drying to obtain the said Form 15;

(2) forming a solution of LY2157299 in ethanol, cooling for crystallization to obtain the said Form 15.

According to the purpose of the present invention, the sixteenth aspect of the present invention is to provide Form 16 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 16, expressed as 2θ angles, has the following characteristic peaks: 9.3°±0.2°, 10.6°±0.2°, 11.9°±0.2°, 13.4°±0.2°, 17.5°±0.2°, 19.0°±0.2°, 19.6°±0.2°, 21.0°±0.2°, 23.3°±0.2°, 23.9°±0.2°, 25.7°±0.2° and 26.2°±0.2°.

Non-restrictively, in one typical embodiment of the present invention, the X-ray powder diffraction pattern of the said Form 16 is shown in FIG. 37.

The present invention provides a preparation method of Form 16, which include the following steps: forming a solution of LY2157299 in acetone, cooling for crystallization, separating crystals and drying to obtain the said Form 16.

According to the purpose of the present invention, the seventeenth aspect of the present invention is to provide Form 17 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 17, expressed as 2θ angles, has the following characteristic peaks: 8.8°±0.2°, 11.7°±0.2°, 12.3°±0.2°, 13.6°±0.2°, 16.8°±0.2°, 17.3°±0.2°, 18.8°±0.2°, 20.0°±0.2°, 20.7°±0.2°, 23.7°±0.2°, 24.0°±0.2° and 24.7°±0.2°.

Non-restrictively, in one typical embodiment of the present invention, the X-ray powder diffraction pattern of the said Form 17 is shown in FIG. 38.

The present invention provides a preparation method of Form 17, which include the following steps: forming a solution of LY2157299 in butanone, cooling for crystallization to obtain the said Form 17.

According to the purpose of the present invention, the eighteenth aspect of the present invention is to provide Form 18 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 18, expressed as 2θ angles, has the following characteristic peaks: 9.1°±0.2°, 9.8°±0.2°, 11.9°±0.2°, 13.6°±0.2°, 15.8°±0.2°, 17.0°±0.2°, 18.9°±0.2°, 19.4°±0.2°, 20.5°±0.2°, 23.9°±0.2°, 24.5°±0.2° and 25.1°±0.2°.

Non-restrictively, in one typical embodiment of the present invention, the X-ray powder diffraction pattern of the said Form 18 is shown in FIG. 39.

The present invention provides a preparation method of Form 18, which include the following steps: forming a solution of LY2157299 in ethyl acetate, cooling for crystallization to obtain the said Form 18.

According to the purpose of the present invention, the nineteenth aspect of the present invention is to provide Form 19 of 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, the X-ray powder diffraction pattern of Form 19, expressed as 2θ angles, has the following characteristic peaks: 8.1°±0.2°, 9.9°±0.2°, 16.5°±0.2°, 17.4°±0.2°, 18.3°±0.2°, 19.1°±0.2°, 20.0°±0.2°, 20.7°±0.2°, 25.0°±0.2° and 25.3°±0.2°.

Non-restrictively, in one typical embodiment of the present invention, the X-ray powder diffraction pattern of the said Form 19 is shown in FIG. 40.

The present invention provides a preparation method of Form 19, which include any one of the following:

(1) forming a suspension of LY2157299 in 1,4-dioxane, stirring for crystallization, separating crystals and drying to obtain the said Form 19;

(2) forming a solution of LY2157299 in 1,4-dioxane, evaporating under reduced pressure to dryness to obtain the said Form 19;

(3) forming a solution of LY2157299 in 1,4-dioxane, adding an anti-solvent, stirring for crystallization, separating crystals and drying to obtain the said Form 19.

According to the purpose of the present invention, the twentieth aspect of the present invention is to provide an amorphous 2-(6-methyl-pyridin-2-yl)-3-(6-amido-quinolin-4-yl)-5,6-dihydro-4h-pyrrolo[1,2-b]pyrazole and its preparation methods.

Using Cu-Kα radiation, non-restrictively, in one typical embodiment of the present invention, the X-ray powder diffraction pattern of the said amorphous form is shown in FIG. 41.

The present invention provides a preparation method of amorphous LY2157299, which includes any one of the following: forming a solution of LY2157299 in acetonitrile, and rotarily evaporating to dryness to obtain the said amorphous form.

In the preparation methods of the present invention, LY2157299 starting material can be known LY2157299, its crystalline forms or its amorphous form, such as but not limited to LY2157299 monohydrate prepared by referencing the methods described in examples of patent document U.S. Pat. No. 7,872,020B2. This document is incorporated herein by reference in its entirety.

The terms used in this invention include:

The $C_3$ to $C_5$ ester includes ethyl formate, methyl acetate, ethyl acetate, isopropyl acetate, propyl acetate, and ethyl propionate.

The $C_3$ to $C_4$ ketone includes acetone and butanone; the $C_1$ to $C_4$ alcohol includes methanol, ethanol, n-propanol, isopropanol, n-butanol, 2-butanol and tert-butanol.

The "co-solvent" refers to a solvent where LY2157299 has a solubility greater than 1 mg/mL, preferably greater than 10 mg/mL, more preferably greater than 100 mg/mL.

The "anti-solvent" refers to a solvent where LY2157299 has a solubility less than 1 mg/mL, preferably less than 0.1 mg/mL, more preferably less than 0.01 mg/mL.

The "room temperature" refers to 10~30° C.

The "stirring" may be performed by routine methods in the field, such as magnetic stirring or mechanical stirring. The stirring speed is 50-1800 r/min, preferably 300-900 r/min.

The "separation" may be performed by routine methods in the field, such as filtration, centrifugation, or volatilization. The preferred method is vacuum filtration, generally at a pressure less than atmospheric pressure at room temperature, preferably less than 0.09 MPa.

The said "drying" may be performed by routine methods in the field, such as room temperature drying, blast drying or vacuum drying. Drying instruments and methods are unrestricted, may be fume hood, blast oven, spray drying, fluidized bed drying or vacuum oven, the pressure may be atmospheric pressure or less than atmospheric pressure, preferably less than 0.09 MPa. Drying temperature can be 10 to 40° C., drying time is 10 to 72 hr, preferably 2 to 24 hr, more preferably 2 to 8 hr.

The "crystalline form" in the present invention is confirmed by the X-ray powder diffraction pattern, having a unique ordered molecular arrangement or configuration within the crystal lattice. It is known to those skilled in the field that experimental errors of X-ray diffraction depend on instrument conditions, sample preparation and sample purity. The 2θ angle of the peaks in the X-ray powder diffraction pattern usually varies slightly due to the difference in the instrument and sample. The differences in peak position may vary by 1°, 0.8°, 0.5°, 0.3°, 0.1° 2θ, depending on different instruments and samples, and usually ±0.2° in differences are allowed. The relative intensities of peaks may change with the change of samples, sample preparation and other experimental conditions; therefore, the order of peak intensities should not be regarded as the only or the determining factor. Due to the effect of experimental factors including sample height, peak position may shift; generally, a small amount of peak shifting is acceptable experimental error. Hence, it is easily understood for those skilled in the field that any LY2157299 having the same or similar X-ray powder diffraction pattern as that of the crystalline form of corresponding forms in the present invention should be within the scope of the present invention. "Pure crystalline form" refers to a pure crystalline form confirmed by X-ray powder diffraction.

The novel crystalline forms of LY2157299 of the present invention is substantially pure and substantially free of any other crystalline or amorphous forms. When "substantially pure" in the present invention referring to a new crystalline form, it means that the new crystalline form comprises at least 80% by weight of the compound present, more preferably at least 90% by weight, especially at least 95% by weight, in particular at least 99% by weight.

According to the purpose of the present invention, the 21th aspect of the present invention provided is a pharmaceutical composition, the uses of the said composition in treating or preventing diseases related to TGF-β; the diseases related to TGF-β include cancers, precancers, kidney diseases, pulmonary fibrosis and eye disease.

The said composition comprises a therapeutically and/or preventively effective amount of one or more novel crystalline forms of LY2157299 of the present invention or LY2157299 salts, and at least one pharmaceutically acceptable carrier; wherein new crystalline forms of LY2157299 include LY2157299 Form 1, LY2157299 Form 2, LY2157299 Form 3, LY2157299 Form 4 and LY2157299 Form 7. Moreover, the pharmaceutical composition may also consist of other acceptable active ingredients, such as other TGF-β inhibitors, anti-proliferation or anti-cancer drugs. According to the present invention, the method for treating humans include administering TGF-β inhibitors. The TGF-β inhibitor can be made into oral, rectal, local and parental such as injection dosage forms, including tablets, powders, capsules, lozenges, emulsions, creams, syrups, sublinguals, small medicine bags, flat capsules, elixirs gels, suspensions, injectable solutions, aerosols, ointments, suppository, or a combination of two or many such forms.

The crystalline forms of compositions of LY2157299 in the present invention can be administered to patients in single dose or separate dose at 0.5 mg/kg to 50 mg/kg. The single dose can have 0.5 mg to about 1000 mg of the said compound. When administered orally, the composition can be administered as pills or capsules containing 0.5 mg to 500 mg of the active ingredient, especially containing 0.5 mg, 1 mg, 5 mg, 10 mg, 15 mg, 20 mg, 25 mg, 50 mg, 75 mg, 80 mg/100 mg, 120 mg, 150 mg, 175 mg, 200 mg and 500 mg, and in a daily dose of 0.5 mg/kg to 40 mg/kg. The actual dose of the active ingredient should depends on many factors, include severity of the disease, patient age, age, physical conditions, gender, the potency and metabolism, administration route, therefore the above dose selection has no meanings to limit the scope of the present invention.

The pharmaceutical compound can contain at least one crystalline forms designated in this invention, mixed with pharmaceutically acceptable excipients to make a composition, and use capsules, small medicine bags, flat capsules, paper or other absorbable container or shelfs or disposable container such as ampules to pack or seal. The excipients can be solid, semi-solid, or liquid. The pharmaceutical composition can use excipients such as starch, sugar, syrup, sorbitol, mannitol, glycol, wax, clay, calcium silicate, silicon dioxide, polyvinylpyrrolidone, calcium phosphate, cocoa butter, ester, oil, Alginate, gel, methyl cellulose, microcrystalline cellulose, lubricant, binder and disintegrant.

The preferred dosage forms are pills, powders, capsules, injectables (solutions), creams, ointments and aerosols.

FIGURE DESCRIPTION

FIG. 1 is the XRPD plot of LY2157299 monohydrate prepared according to U.S. Pat. No. 7,872,020B2.

FIG. 2 is the DSC plot of LY2157299 monohydrate prepared according to U.S. Pat. No. 7,872,020B2.

FIG. 3 is the TGA plot of LY2157299 monohydrate prepared according to U.S. Pat. No. 7,872,020B2.

FIG. 4 is the isothermal sorption plot of LY2157299 monohydrate prepared according to U.S. Pat. No. 7,872,020B2.

FIG. 5 is the PLM plot of LY2157299 monohydrate prepared according to U.S. Pat. No. 7,872,020B2.

SPECIFIC IMPLEMENTATIONS

The following examples will help to further understand the present invention, but are not intended to limit the contents of the present invention.

Instruments and characterization methods:

X-ray powder diffraction (XRPD): performed on Bruker D8 Advance diffractometer. Samples were tested at room temperature. Testing conditions: 2θ scan range 3-40°, step size 0.02°, and speed 0.2s/step.

Polarized light microscopy (PLM) plots were collected on XP-500E polarized light microscopy. Took a small amount of powder sample on a glass and added some mineral oil, covered with the cover glass, placed it on the stage for observation and took a picture.

Differential thermal analysis data were collected on TA Instruments Q200 DSC. Method: A sample of 1 to 10 mg was placed in an aluminum pan with a pin-holed lid, and the sample was heated from room temperature to 200° C. at a heating rate of 10° C./min under the protection of dry nitrogen purge at 40 mL/min.

Thermogravimetric analysis data were collected on TA Instruments Q500 TGA. Method: A sample of 5 to 15 mg was placed in a platinum pan, using High Resolution™, the sample was heated from room temperature to 350° C. at a heating rate of 10° C./min under the protection of dry nitrogen purge at 40 mL/min.

Dynamic vapor sorption data and isothermal sorption data were collected on TA Instruments Q5000 TGA. Method: A sample of 1 to 10 mg was placed in a platinum pan; the weight change of the sample during the change in relative humidity from 0% to 80% to 0% was measured.

1H Nuclear magnetic resonance spectrum (1H-NMR) data were collected on Bruker Avance II DMX 500 MHz nuclear magnetic resonance spectrometer. Method: place 1 mg to 5 mg sample and dissolve it into a nuclear magnetic sample tube with 0.5 mL deuterated reagent for detection.

The PLM used is model XR-500E, optical lens 10×, subject lens 10×. Place some samples in a slide, add one drop of silica oil, place a cover slip and observe.

Unless particularly specified, all reagents used in the Examples were commercially available.

Unless particularly specified, all Examples were operated at room temperature.

Preparation Example 1

Preparing_LY2157299monohydrate

LY2157299 monohydrate was obtained according to Example 1 in U.S. Pat. No. 7,872,020B2.

$^1$H-NMR (CDCl$_3$):δ=9.0 ppm (d,4.4 Hz, 1H); 8.23-8.19 ppm (m, 2H); 8.315 ppm (dd, 1.9 Hz, 8.9 Hz, 1H); 7.455 ppm (d, 4.4 Hz, 1H); 7.364 ppm (t, 7.7 Hz, 1H); 7.086 ppm (d, 8.0 Hz, 1H); 6.969 ppm (d, 7.7 Hz, 1H); 6.022 ppm (m, 1H); 5.497 ppm (m, 1H); 4.419 ppm (d, 7.3 Hz, 2H); 2.999 ppm (m, 2H); 2.770 ppm (p, 7.2 Hz, 7.4 Hz, 2H); 2.306 ppm (s, 3H); 1.817 ppm (m, 2H). MS ES$^+$: 370.2; Exact: 369.16.

Figure 1:
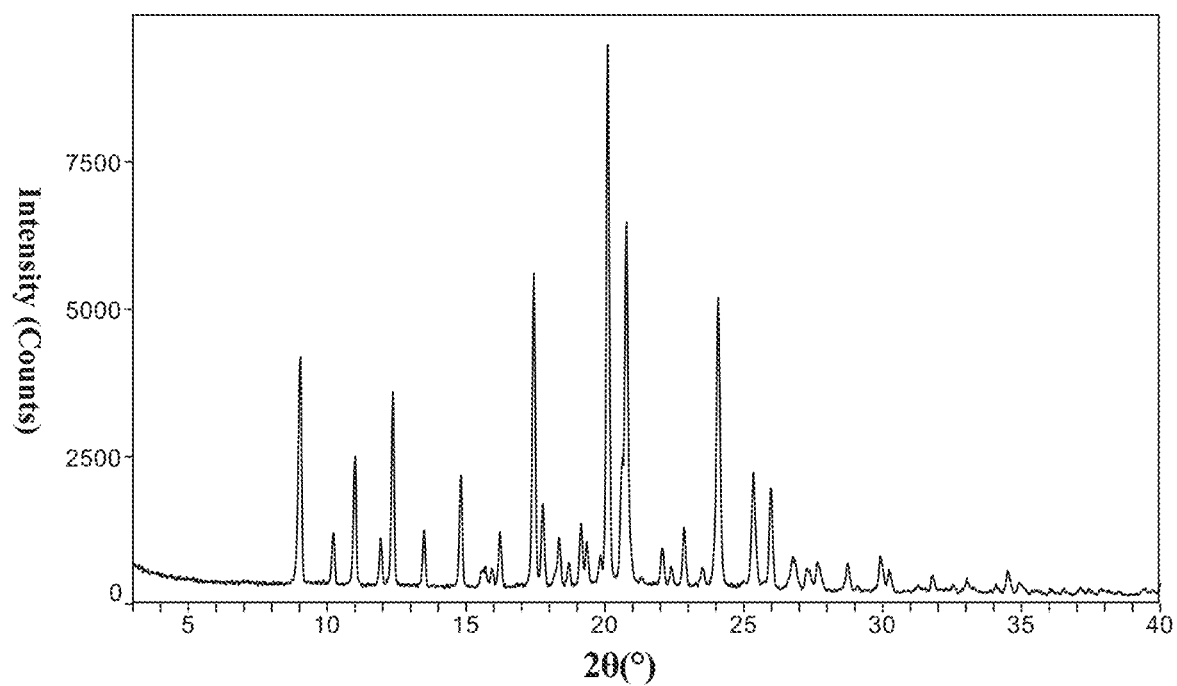

Its XRPD plot is shown in FIG. 1, and its peak lists are accordant with that of the monohydrate of U.S. Pat. No. 7,872,020B2.

Figure 2:
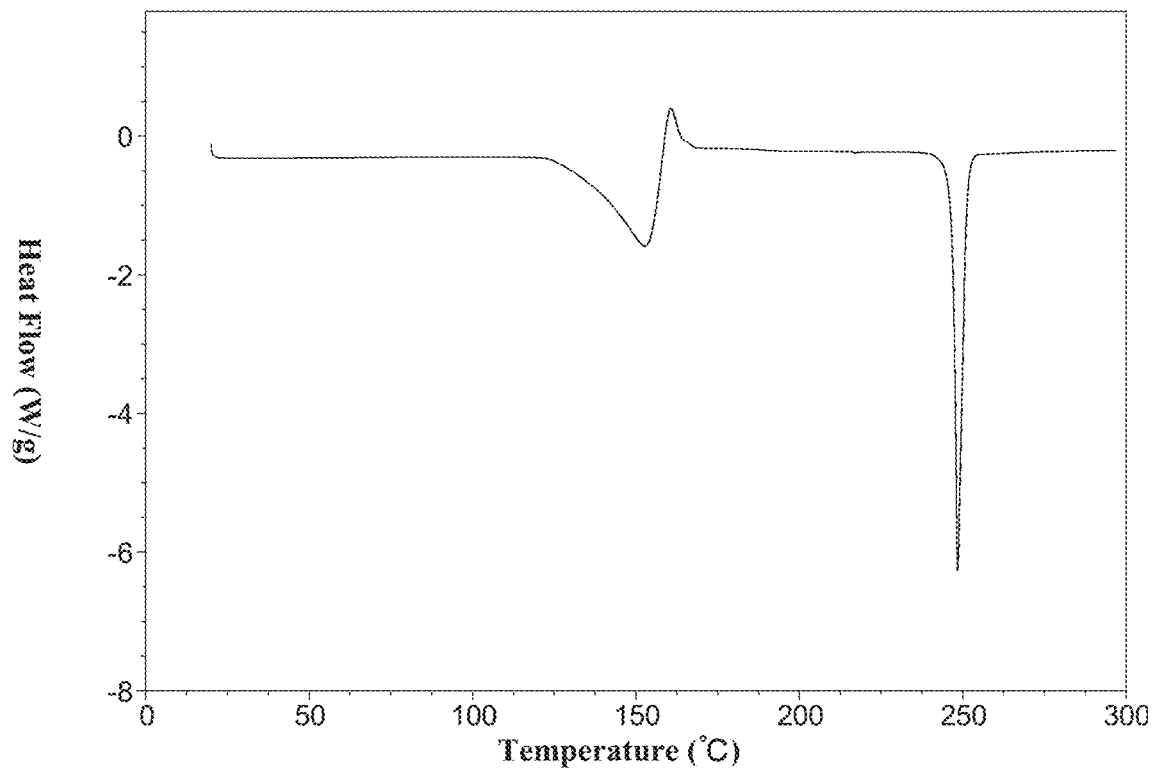

Its DSC plot is shown in FIG. 2: dehydrated at 133° C. and stated phase transition, after phase transition it melted at 247° C.

Figure 3:
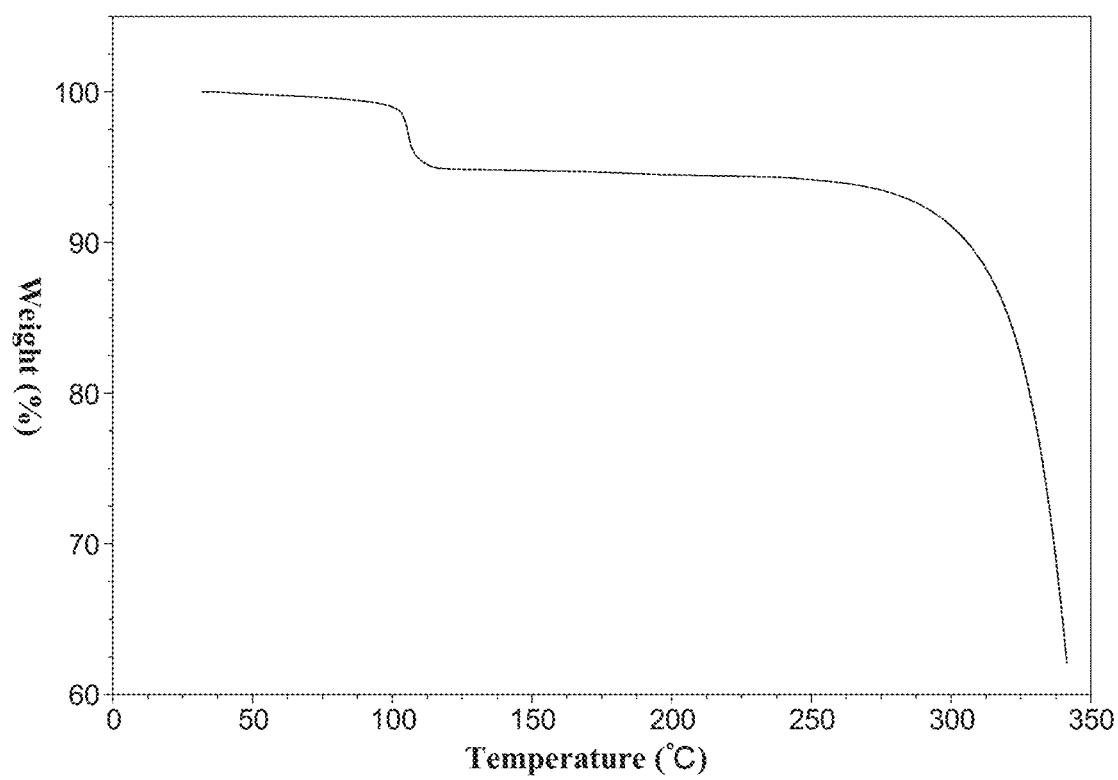

Its TGA plot is shown in FIG. 3: 4.7% step-wise weight loss at 80° C.~120° C., eq. to about one mole of water, decomposes at 323° C.

Figure 4:
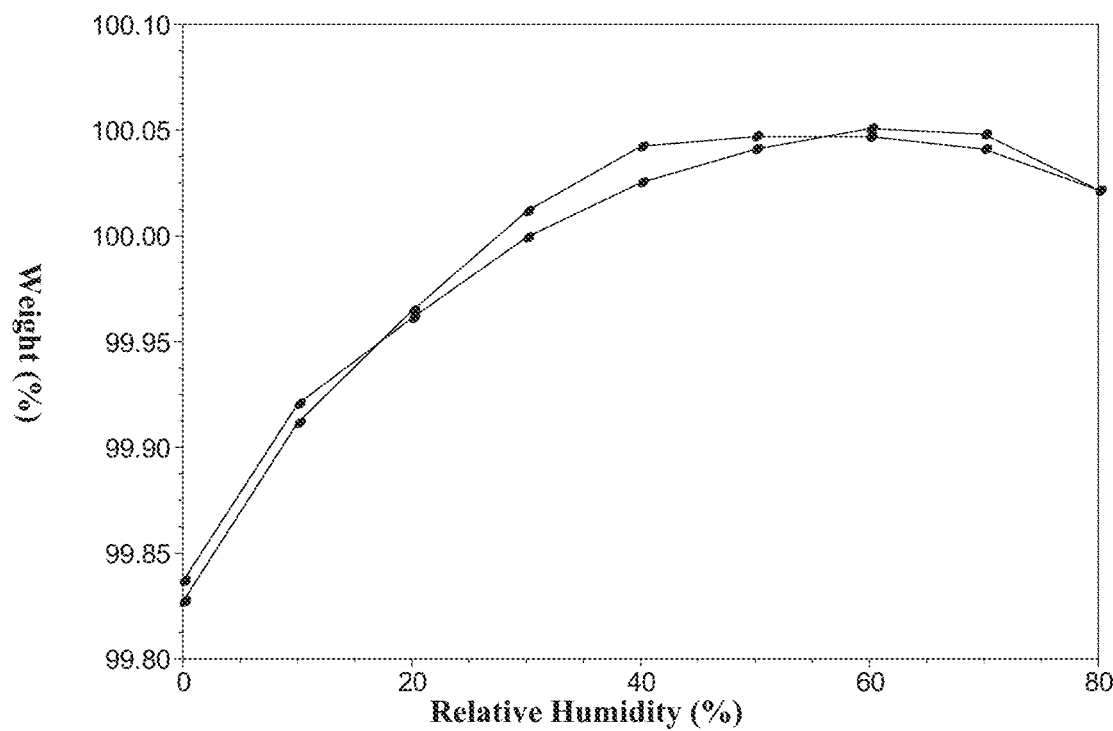

Its isothermal sorption plot is shown in FIG. 4: weight change from 0% RH ~80% RH is 0.22%, greater than 0.2%, slightly hygroscopic.

Figure 5:
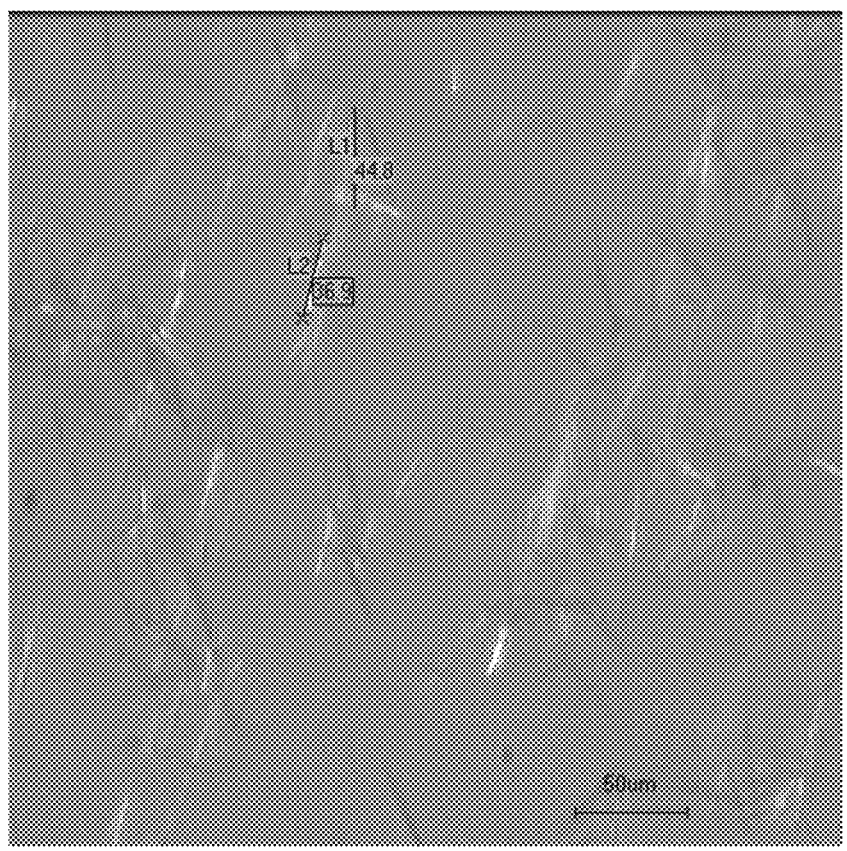

Its PLM plot is shown in FIG. 5: needle like tiny crystals.

Example 1

Took 20 mg of LY2157299 monohydrate in Preparation Example 1, added 0.5 mL of acetone to dissolve to obtain a clear solution, dropwisely added it to 2 mL pre-chilled diisopropyl ether, stir at 5° C. for 2 hours to precipitate crystals, centrifuged, dried and room temperature to obtain 14 mg LY2157299 Form 1, yield 73%.

Figure 6:
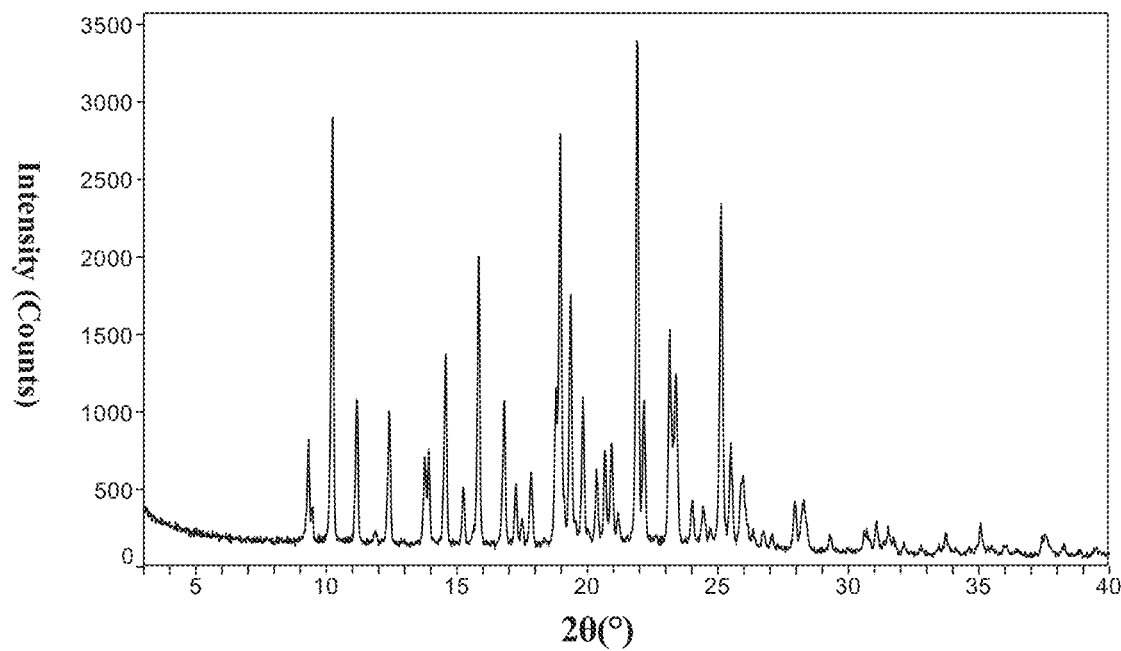
FIG. 6 is the XRPD plot of LY2157299 Form 1 of the present invention.
Figure 7:
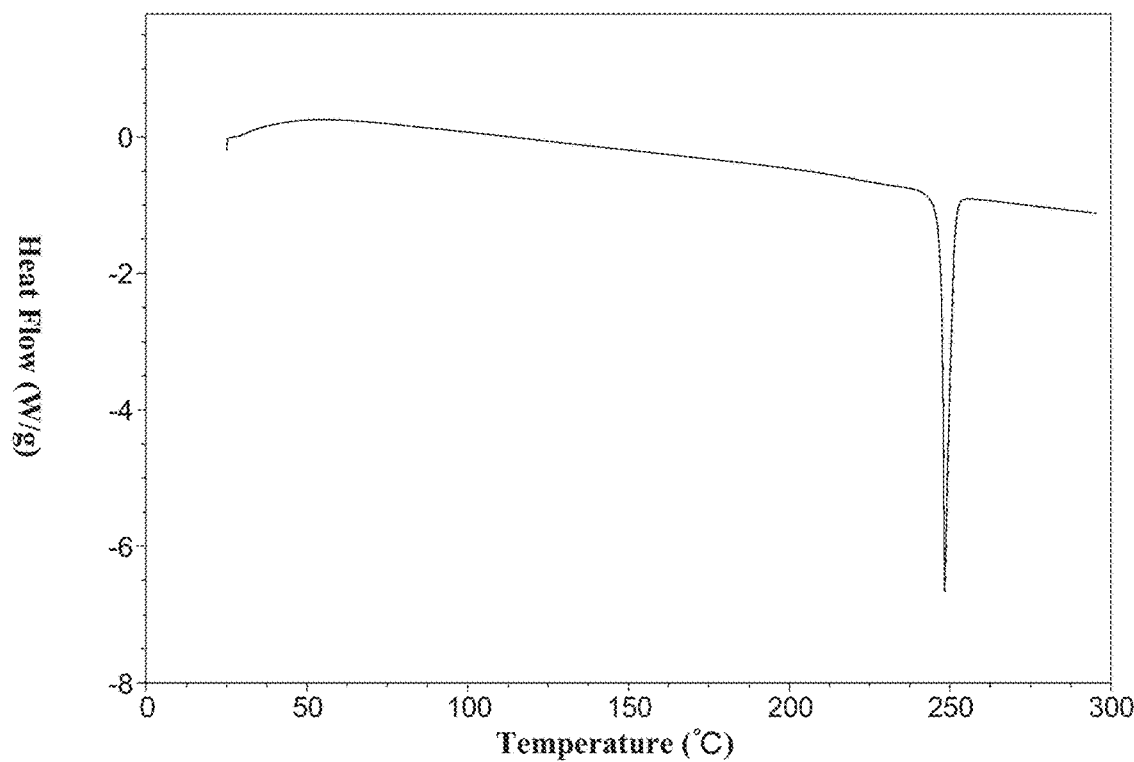
FIG. 7 is the DSC plot of LY2157299 Form 1 of the present invention.
Figure 8:
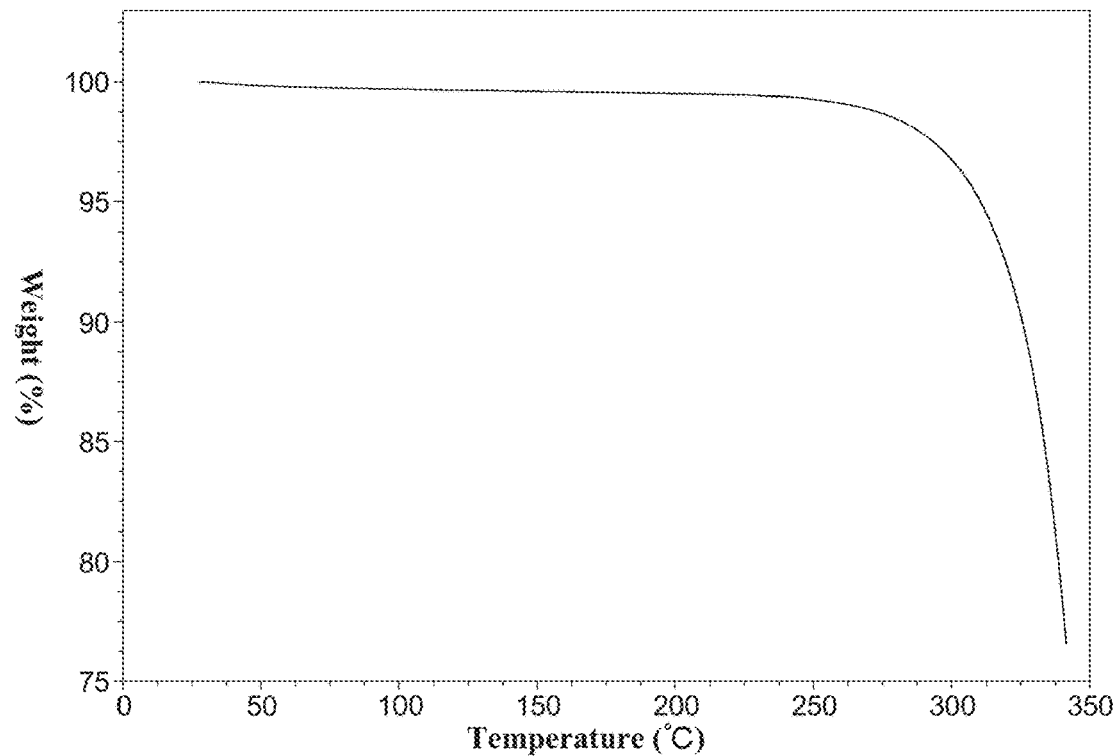
FIG. 8 is the TGA plot of LY2157299 Form 1 of the present invention.
Figure 9:
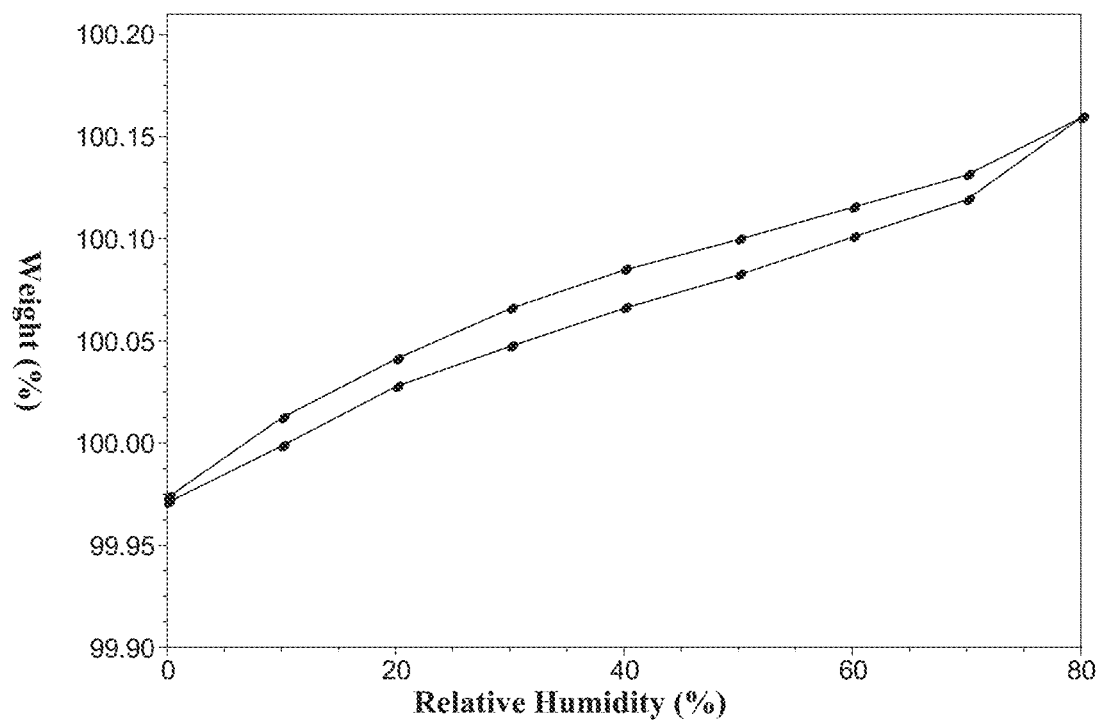
FIG. 9 is the isothermal sorption plot of LY2157299 Form 1 of the present invention.

Its XRPD plot is shown in FIG. 6.
Its DSC thermogram is shown in FIG. 7.
Its TGA thermogram is shown in FIG. 8.
Its isothermal sorption curve is shown in FIG. 9.

Example 2

Took 20 mg of LY2157299 monohydrate in Preparation Example 1, added 4 mL of butanone to dissolve to obtain a clear solution, dropwisely added it to 12 mL pre-chilled methyl tert-butyl ether, stir at 5° C. to precipitate crystals for 0.5 hour, centrifuged, dried and room temperature to obtain 10 mg LY2157299 Form 1, yield 52%.

Example 3

Took 20 mg of LY2157299 monohydrate in Preparation Example 1, added 4 mL of acetone to dissolve to obtain a clear solution, dropwisely added it to 20 mL pre-chilled ethyl ether, stir at 0° C. for 0.5 hour to precipitate crystals, centrifuged, dried and room temperature to obtain 12 mg LY2157299 Form 1, yield 63%.

Example 4

Took 20 mg of LY2157299 monohydrate in Preparation Example 1, added 1 mL of butanone to dissolve to obtain a clear solution, dropwisely added it to 2 mL pre-chilled diisopropyl ether, stir at 0° C. for 1 hour, centrifuged, dried and room temperature to obtain 9 mg LY2157299 Form 1, yield 47%.

Example 5

Took 10 mg LY2157299 monohydrate in Preparation Example 1, heated at 1° C./min to 130° C., isothermal for 5 min, cooled at 1° C./min to room temperature to obtain 8 mg LY2157299 Form 1, yield 84%.

Example 6

Took 200 mg LY2157299 monohydrate in Preparation Example 1, heated at 10° C./min to 180° C., isothermal for 3 min, cooled at 10° C./min to room temperature to obtain 168 mg LY2157299 Form 1, yield 88%.

Example 7

Took 100 mg LY2157299 monohydrate in Preparation Example 1, heated at 50° C./min to 150° C., isothermal for 10 min, cooled at 50° C./min to room temperature to obtain 77 mg LY2157299 Form 1, yield 81%.

Example 8

Took 1 g LY2157299 monohydrate in Preparation Example 1, heated at 30° C./min to 150° C., isothermal for 5 min, cooled at 30° C./min to room temperature to obtain 0.79 g LY2157299 Form 1, yield 83%.

XRPD patterns, DSC plots, isothermal sorption plots, TGA plots (not shown) of the samples prepared in Examples 2 to 8 are the same as or similar to that of the sample prepared in Example 1, indicating the crystalline forms obtained in Examples 2 to 8 are the same as that of Example 1.

Example 9

Took 10 mg LY2157299 monohydrate in Preparation Example 1, added 4 mL of isopropanol to dissolve to obtain a clear solution, evaporated open-capped at 25° C. to dryness to obtain 8 mg LY2157299 Form 2, yield 84%.

Figure 10:
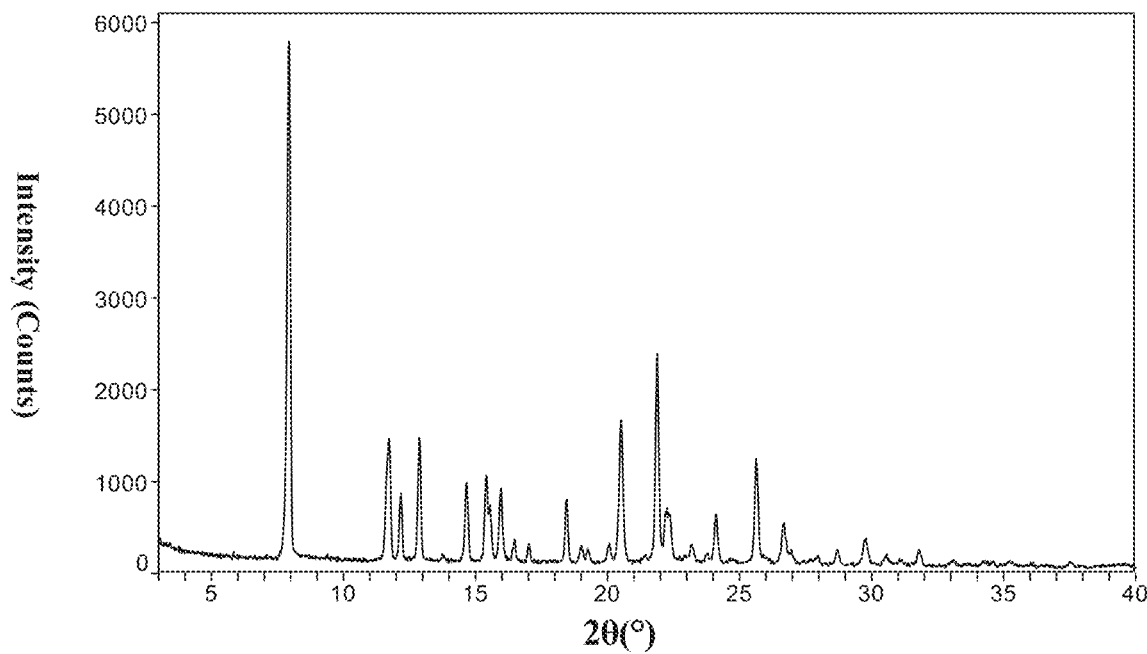
FIG. 10 is the XRPD plot of LY2157299 Form 2 of the present invention.
Figure 11:
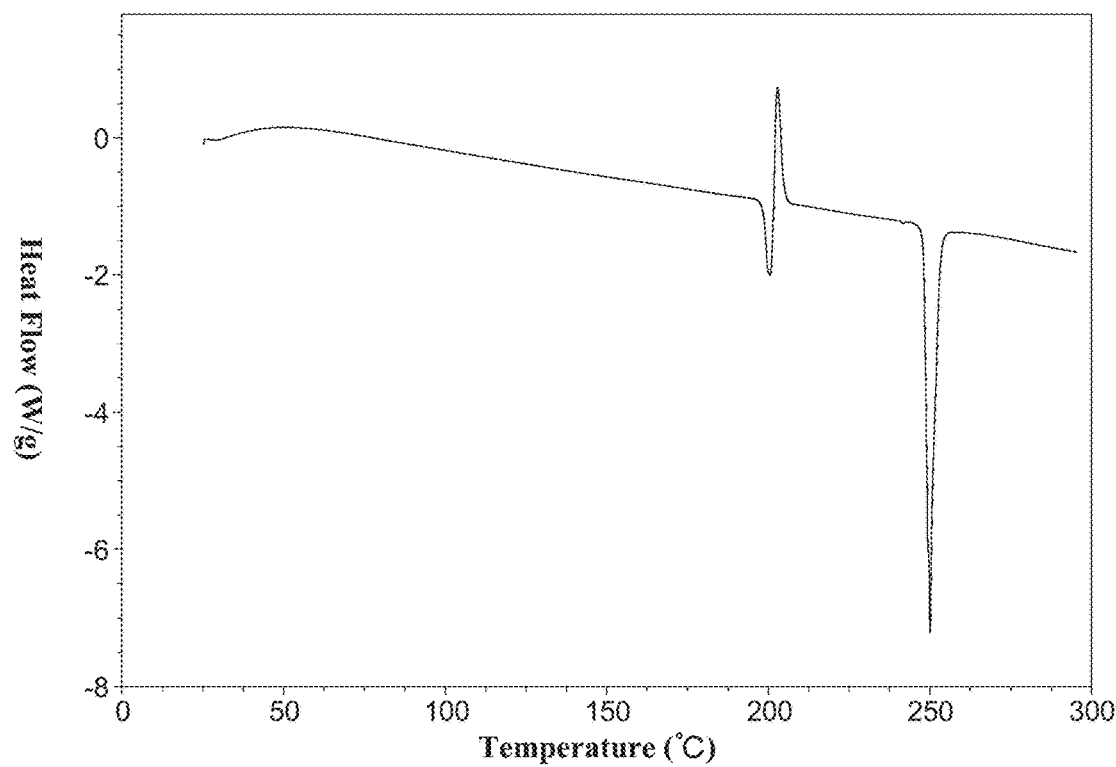
FIG. 11 is the DSC plot of LY2157299 Form 2 of the present invention.
Figure 12:
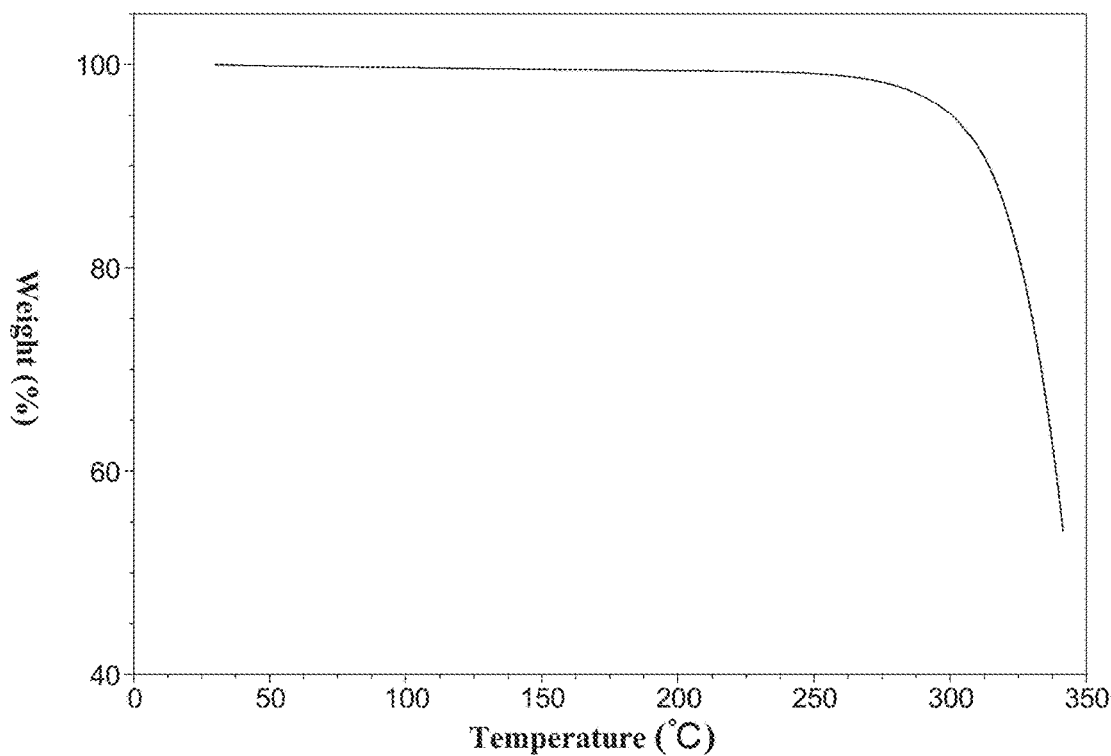
FIG. 12 is the TGA plot of LY2157299 Form 2 of the present invention.
Figure 13:
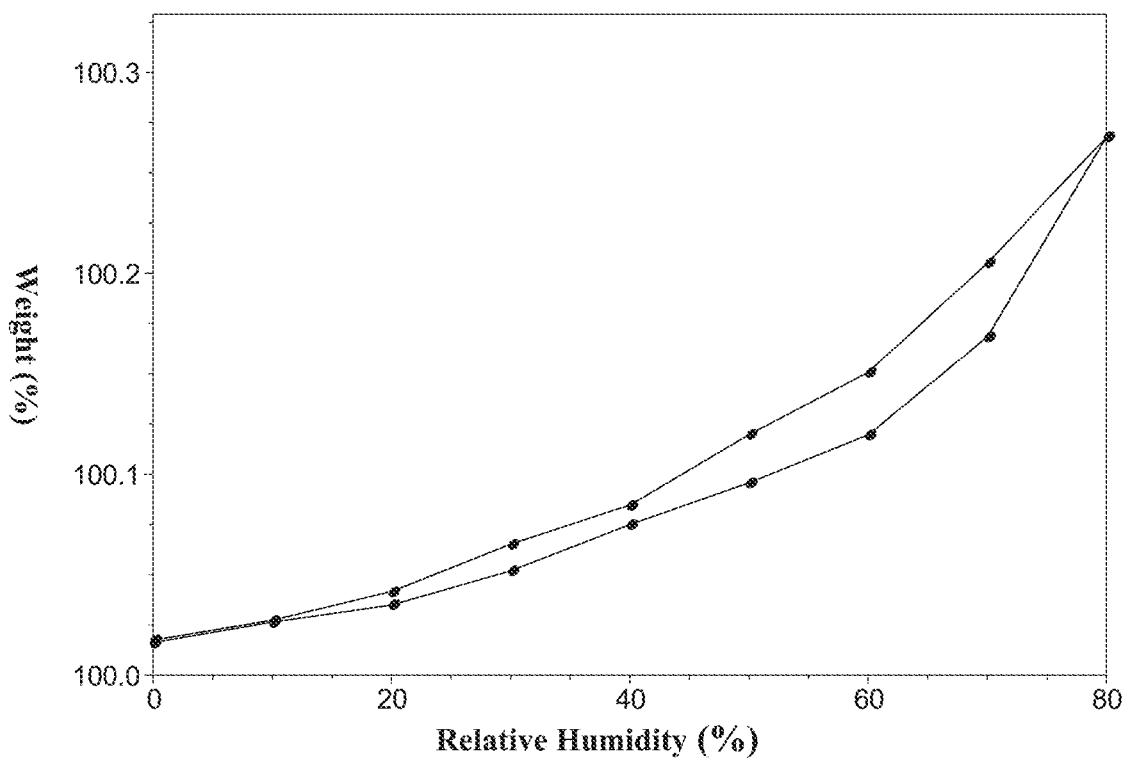
FIG. 13 is the isothermal sorption plot of LY2157299 Form 2 of the present invention.

Its XRPD plot is shown in FIG. 10.
Its DSC thermogram is shown in FIG. 11.
Its TGA thermogram is shown in FIG. 12.
Its isothermal sorption curve is shown in FIG. 13.

Example 10

Took 20 mg of the LY2157299 monohydrate of Preparation Example 1, added 1.6 mL isopropanol to dissolve to obtain a clear solution, evaporated at 40° C. to dryness to obtain 16 mg LY2157299 Form 2, yield 84%.

Example 11

Took 10 mg of the LY2157299 monohydrate of Preparation Example 1, added 2 mL n-propanol to dissolve to obtain a clear solution, evaporated at reduced pressure at 30° C. to dryness to obtain 7 mg LY2157299 Form 2, yield 73%.

Example 12

LY2157299 Form 2 can also be obtained by replacing the solvents, the amount of solvents, evaporation temperature, and evaporation methods in Example 9 with the following table.

| No. | Solvent | Amount of Solvent/mL | Tem. | Evap. Method |
| --- | --- | --- | --- | --- |
| Exp. 1 | n-Propanol | 0.8 | 25° C. | Atmospheric |
| Exp. 2 | n-Propanol | 0.8 | 40° C. | Atmospheric |
| Exp. 3 | THF | 0.8 | 40° C. | Atmospheric |
| Exp. 4 | Isopropyl acetate/THF | 0.6/0.3 | 40° C. | Atmospheric |
| Exp. 5 | THF | 1.4 | 25° C. | Reduced pressure |

Example 13

Took 15 mg of the LY2157299 Form 1 of Example 8, added 0.3 mL tetrahydrofuran to obtain a suspension, stirred at 25° C. for 6 days, filtrated, then blast dried at room temperature for 1 hour to obtain 10 mg LY2157299 Form 2, 67% yield.

Example 14

Took 30 mg of the LY2157299 Form 1 of Example 8, added 0.3 mL tetrahydrofuran to obtain a suspension, stirred at 25° C. for 3 days, filtrated, then blast dried at room temperature for 1 hour to obtain 23 mg LY2157299 Form 2, 77% yield.

Example 15

Took 20 mg of the LY2157299 Form 1 of Example 8, added 1 mL isopropyl acetate and 1 ml toluene to obtain a suspension, stirred at 40° C. for 7 days, filtrated, then blast dried at room temperature for 1 hour to obtain 12 mg LY2157299 Form 2, 60% yield.

Example 16

Took 30 mg of the LY2157299 Form 1 of Example 8, added 0.3 mL isopropyl acetate and 0.3 ml toluene to obtain a suspension, stirred at 60° C. for 3 days, filtrated, then blast dried at room temperature for 1 hour to obtain 23 mg LY2157299 Form 2, 77% yield.

Example 17

Took 20 mg of the LY2157299 Form 1 of Example 8, added 0.5 mL isopropyl acetate and 0.5 ml toluene to obtain a suspension, stirred at 25° C. for 7 days, filtrated, then blast dried at room temperature for 1 hour to obtain 13 mg LY2157299 Form 2, 65% yield.

Example 18

Took 20 mg of the LY2157299 monohydrate of Preparation Example 1, at 50° C., added 1 mL tetrahydrofuran to obtain a solution, stirred at 5° C. for 0.5 hour, filtrated, then vacuum dried at room temperature for 1 hour to obtain 12 mg LY2157299 Form 2, 63% yield.

Example 19

Took 30 mg of the LY2157299 monohydrate of Preparation Example 1, at 55° C., added 1 mL tetrahydrofuran to obtain a solution, stirred at 0° C. for 5 hours, filtrated, then vacuum dried at room temperature for 1 hour to obtain 21 mg LY2157299 Form 2, 73% yield.

Example 20

Took 20 mg of the LY2157299 monohydrate of Preparation Example 1, at 50° C., added 1 mL tetrahydrofuran to obtain a solution, stirred at 25° C. for 5 hours, filtrated, then vacuum dried at room temperature for 1 hour to obtain 11 mg LY2157299 Form 2, 58% yield.

XRPD patterns, DSC plots, isothermal sorption plots, TGA plots (not shown) of the samples prepared in Examples 10 to 20 are the same as or similar to that of the sample prepared in Example 9, indicating the crystalline forms obtained in Examples 10 to 20 are the same as that of Example 9.

Example 21

Took 30 mg LY2157299 monohydrate of Preparation Example 1, added 1.5 mL of acetonitrile to dissolve to obtain a clear solution, evaporated at reduced pressure at 30° C. to dryness to obtain 25 mg LY2157299 Form 3, yield 87%.

Figure 14:
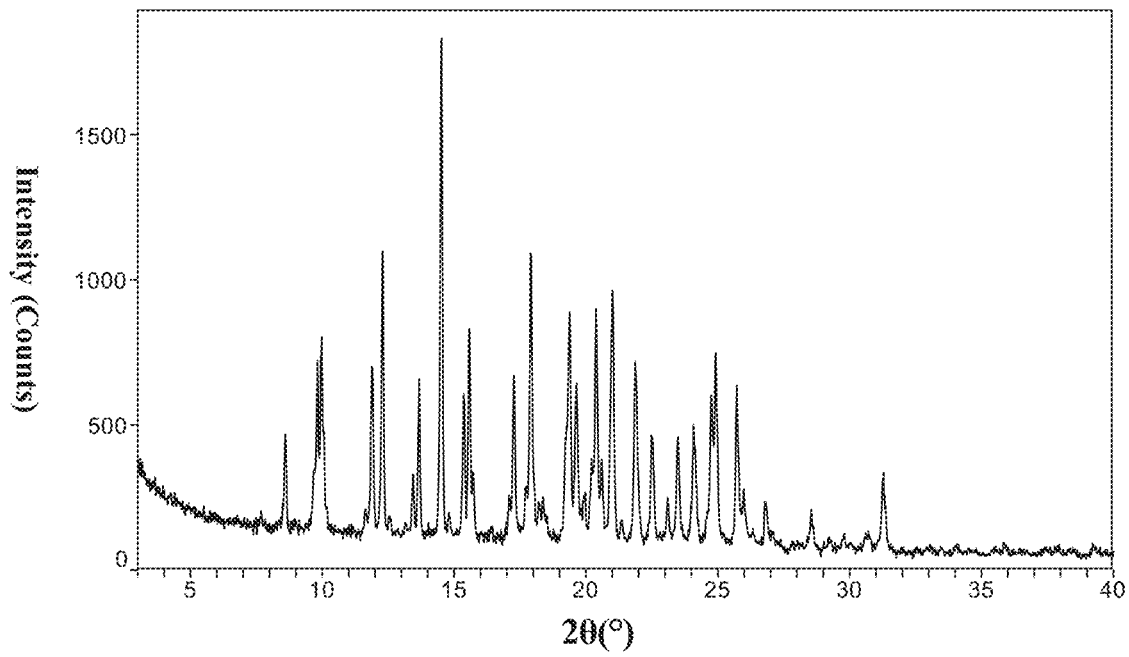
FIG. 14 is the XRPD plot of LY2157299 Form 3 of the present invention.
Figure 15:
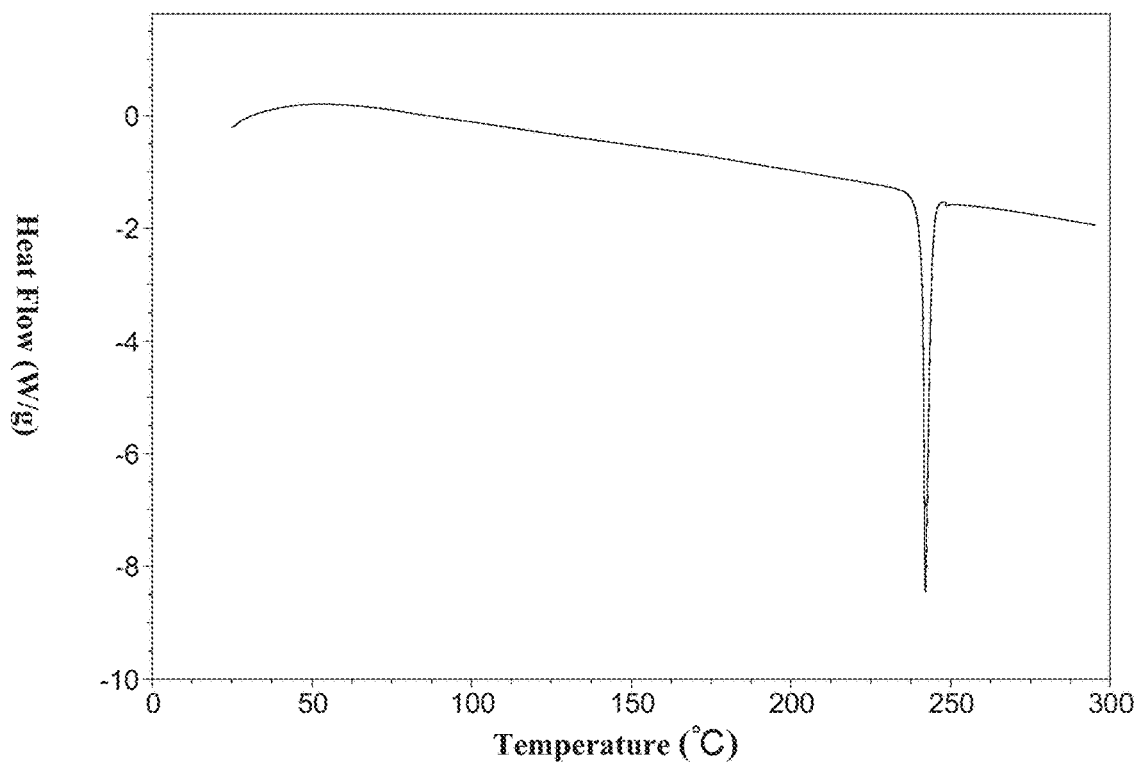
FIG. 15 is the DSC plot of LY2157299 Form 3 of the present invention.
Figure 16:
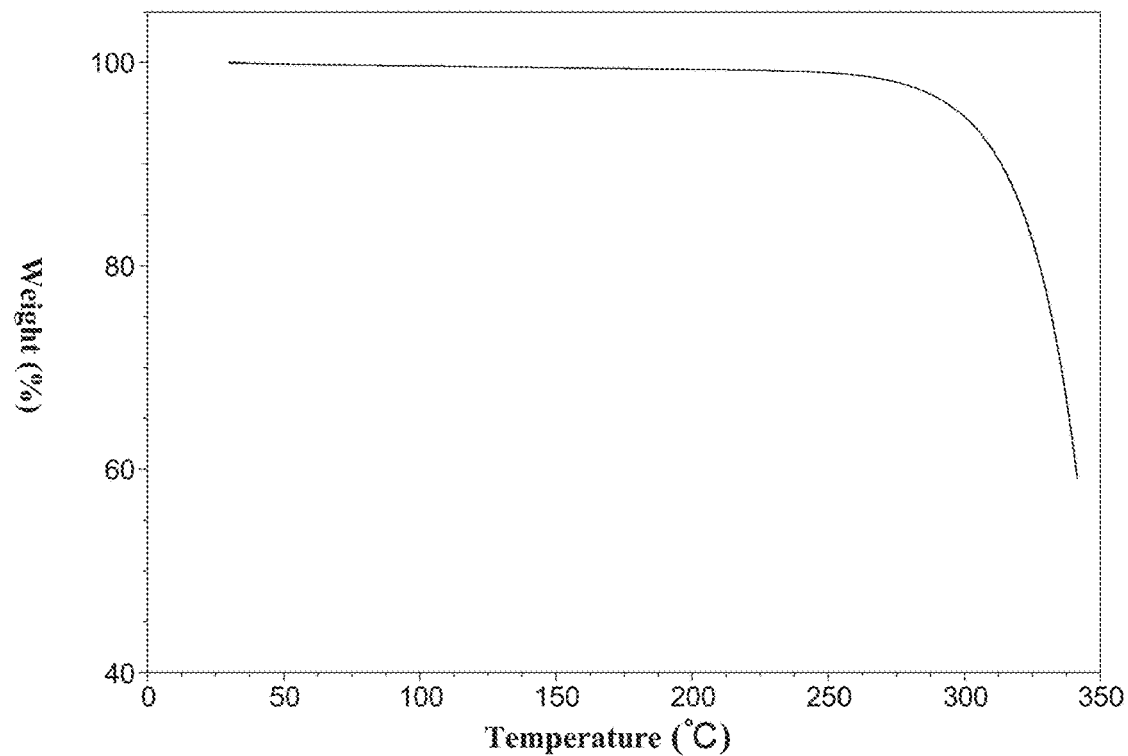
FIG. 16 is the TGA plot of LY2157299 Form 3 of the present invention.
Figure 17:
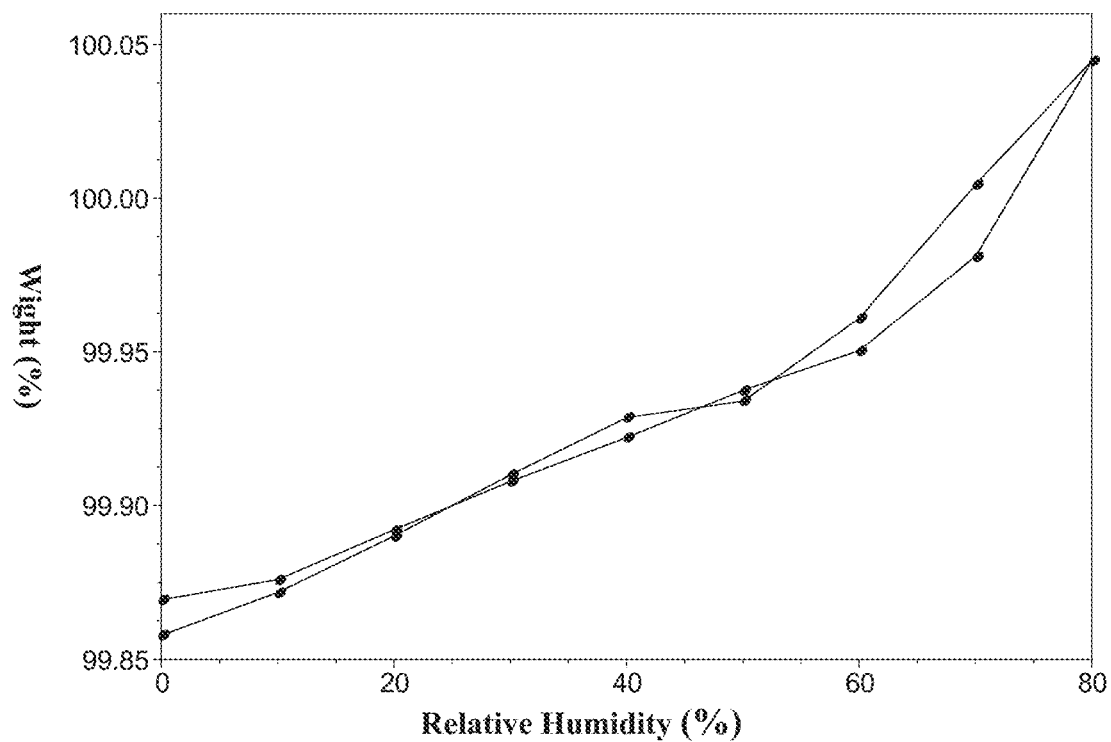
FIG. 17 is the isothermal sorption plot of LY2157299 Form 3 of the present invention.

Its XRPD plot is shown in FIG. 14.
Its DSC thermogram is shown in FIG. 15.
Its TGA thermogram is shown in FIG. 16.
Its isothermal sorption curve is shown in FIG. 17.

Example 22

Took 5 mg LY2157299 monohydrate of Preparation Example 1, added 2 mL of acetonitrile to dissolve to obtain a clear solution, evaporated at reduced pressure at 30° C. to dryness to obtain 3 mg LY2157299 Form 3, yield 63%.

Example 23

Took 100 mg LY2157299 monohydrate of Preparation Example 1, added 10 mL of acetonitrile to dissolve to obtain a clear solution, evaporated at reduced pressure at 40° C. to dryness to obtain 90 mg LY2157299 Form 3, yield 94%.

Example 24

Took 30 mg LY2157299 Form 1 of Example 8, added 0.6 mL of ethyl acetate to obtain a suspension, stirred at room temperature for precipitation for 7 days, filtrated, blast dried at room temperature for 1 hour to obtain 25 mg LY2157299 Form 3, yield 83%.

Example 25

Took 50 mg LY2157299 Form 1 of Example 8, added 0.5 mL of acetonitrile to obtain a suspension, stirred at room temperature for precipitation for 3 days, filtrated, blast dried at room temperature for 1 hour to obtain 44 mg LY2157299 Form 3, yield 88%.

Example 26

Took 30 mg LY2157299 Form 1 of Example 8, added 0.6 mL of acetonitrile to obtain a suspension, stirred at 40° C. for precipitation for 3 days, filtrated, blast dried at room temperature for 1 hour to obtain 23 mg LY2157299 Form 3, yield 77%.

Example 27

Took 15 mg of the LY2157299 Form 1 of Example 8, added 0.6 mL acetone and 0.6 ml methyl tert-butyl ether to obtain a suspension, stirred at 4° C. for 7 days, filtrated, then blast dried at room temperature for 1 hour to obtain 10 mg LY2157299 Form 3, 67% yield.

Example 28

Took 10 mg of the LY2157299 Form 1 of Example 8, added 1 mL methyl acetate to obtain a suspension, stirred at 25° C. for 7 days, filtrated, then blast dried at room temperature for 1 hour to obtain 6 mg LY2157299 Form 3, 60% yield.

Example 29

LY2157299 Form 3 can also be obtained by replacing the solvents, the amount of solvents, and stirring temperature in Example 24 with the following table.

| No. | Solvent | Amount of Solvent/mL | Tem. |
|---|---|---|---|
| Exp. 1 | Ethyl formate | 0.8 | 25° C. |
| Exp. 2 | Acetone/diisopropyl ether | 0.8 | 40° C. |
| Exp. 3 | Acetone/diisopropyl ether | 0.8 | 40° C. |
| Exp. 4 | Butanone/MTBE | 0.6/0.3 | 40° C. |
| Exp. 5 | Butanone/ethyl ether | 1.4 | 25° C. |

Example 30

Took 20 mg of the LY2157299 monohydrate of Preparation Example 1, at 50° C., added 2 mL acetonitrile to form a solution, stirred at 5° C. for 1 hour, filtrated, then vacuum dried at room temperature for 1 hour to obtain 10 mg LY2157299 Form 3, 52% yield.

Example 31

Took 20 mg of the LY2157299 monohydrate of Preparation Example 1, at 55° C., added 1 mL acetonitrile and 0.2 mL ethyl acetate to form a solution, stirred at 0° C. for 3 hours, filtrated, then vacuum dried at room temperature for 1 hour to obtain 12 mg LY2157299 Form 3, 63% yield.

Example 32

Took 30 mg of the LY2157299 monohydrate of Preparation Example 1, at 50° C., added 1.3 mL acetonitrile and 0.2 mL MTBE to form a solution, stirred at 5° C. for 3 hours, filtrated, then vacuum dried at room temperature for 1 hour to obtain 20 mg LY2157299 Form 3, 70% yield.

Example 33

Took 50 mg of the LY2157299 monohydrate of Preparation Example 1, at 50° C., added 1 mL acetonitrile to form a solution, stirred at 0° C. for 2 hours, filtrated, then vacuum dried at room temperature for 1 hour to obtain 28 mg LY2157299 Form 3, 59% yield.

Example 34

Took 20 mg of the LY2157299 monohydrate of Preparation Example 1, added 4 mL ethyl acetate and 0.2 mL ethyl acetate to form a clear solution, at 5° C., added 4 mL diisopropyl ether, stirred for 0.5 hour for crystallization, filtrated, then vacuum dried at room temperature for 2 hour to obtain 10 mg LY2157299 Form 3, 52% yield.

Example 35

Took 20 mg of the LY2157299 monohydrate of Preparation Example 1, added 1 mL acetonitrile to form a clear solution, at 0° C., added 4 mL diisopropyl ether, stirred for 2 hours for crystallization, filtrated, then vacuum dried at room temperature for 2 hours to obtain 15 mg LY2157299 Form 3, 79% yield.

Example 36

Took 40 mg of the LY2157299 monohydrate of Preparation Example 1, added 4 mL ethyl acetate to form a clear solution, at 0° C., added 10 mL diisopropyl ether, stirred for 1 hour for crystallization, filtrated, then vacuum dried at room temperature for 1 hour to obtain 19 mg LY2157299 Form 3, 50% yield.

XRPD patterns, DSC plots, isothermal sorption plots, TGA plots (not shown) of the samples prepared in Examples 22 to 36 are the same as or similar to that of the sample prepared in Example 21, indicating the crystalline forms obtained in Examples 22 to 36 are the same as that of Example 21.

Example 37

Took 150 mg of the LY2157299 Form 1 of Example 8, added 3 mL methanol to form a suspension, stirred at 25° C. for 7 days for crystallization, filtrated, then blast dried at room temperature for 1 hour to obtain 120 mg LY2157299 Form 4, 80% yield.

Figure 18:
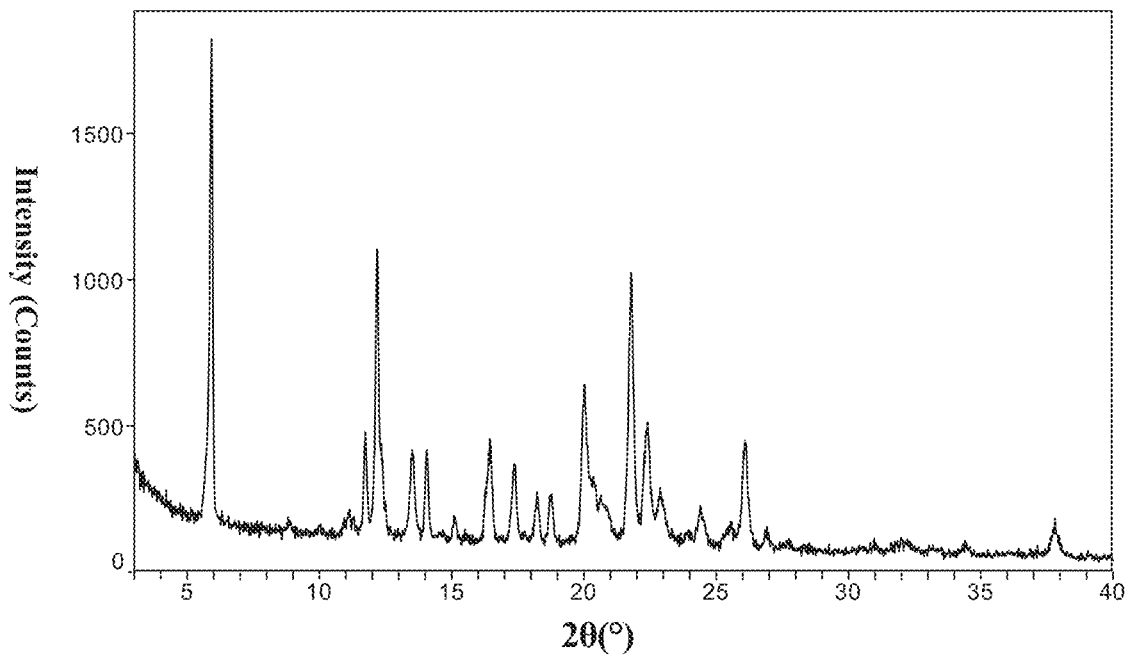
FIG. 18 is the XRPD plot of LY2157299 Form 4 of the present invention.
Figure 19:
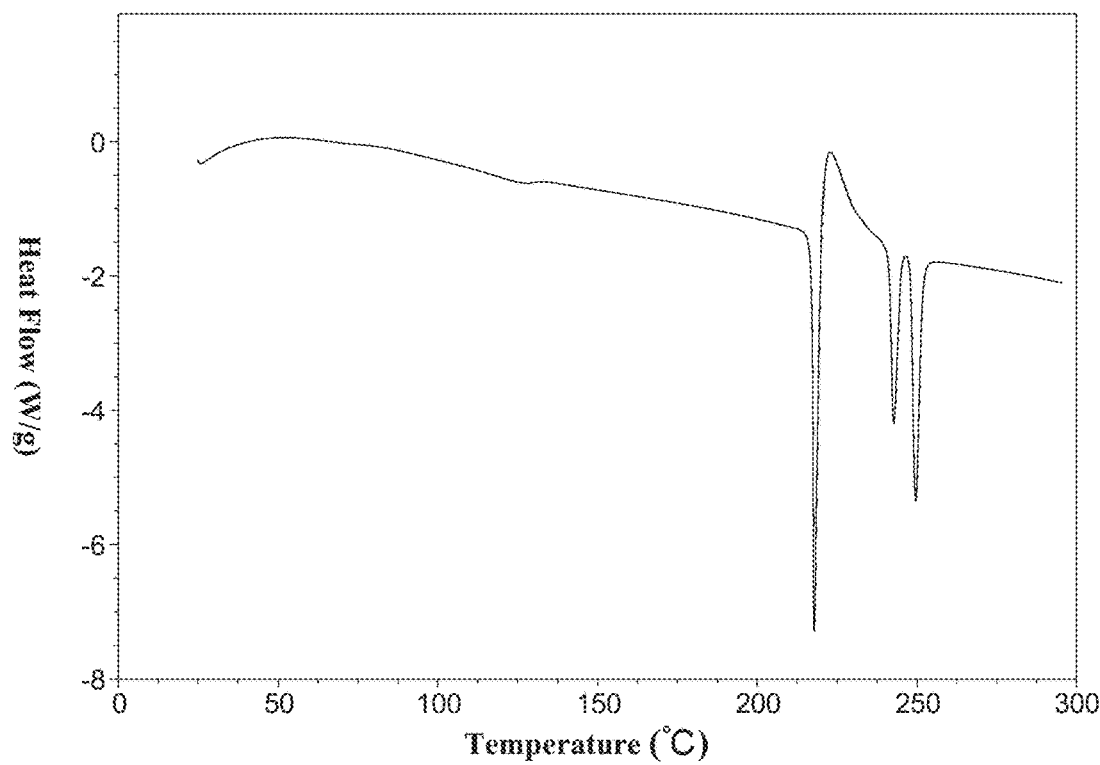
FIG. 19 is the DSC plot of LY2157299 Form 4 of the present invention.
Figure 20:
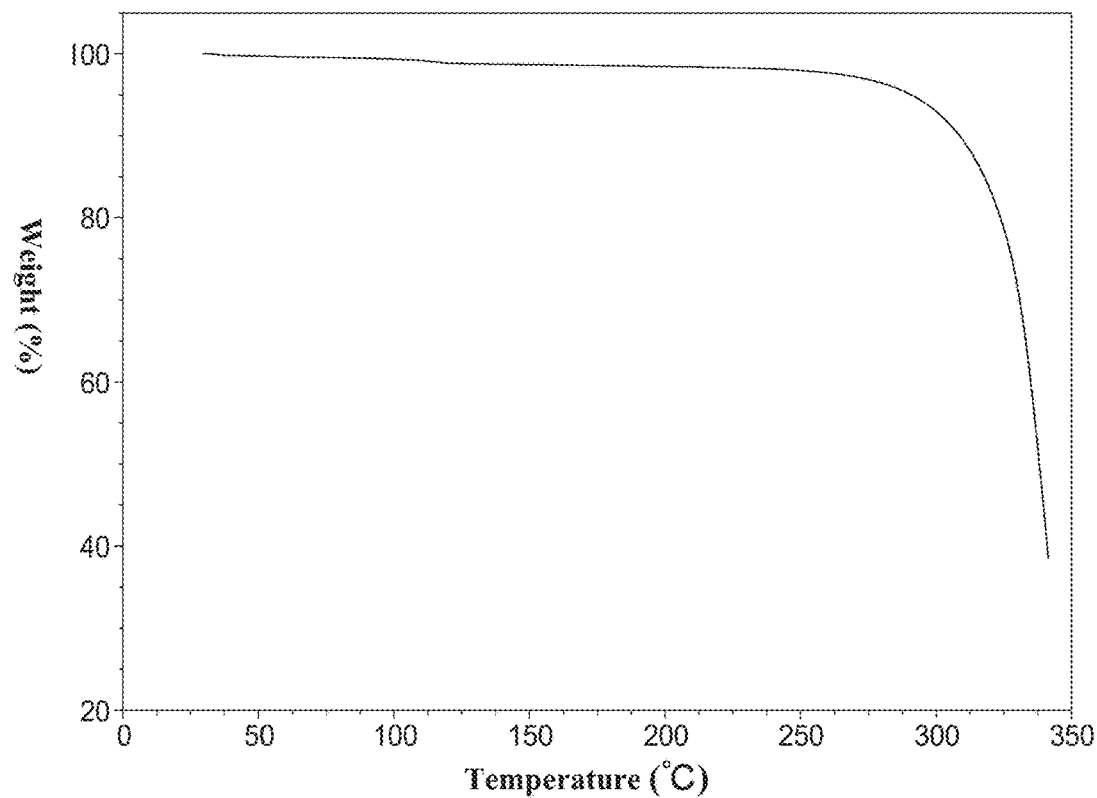
FIG. 20 is the TGA plot of LY2157299 Form 4 of the present invention.
Figure 21:
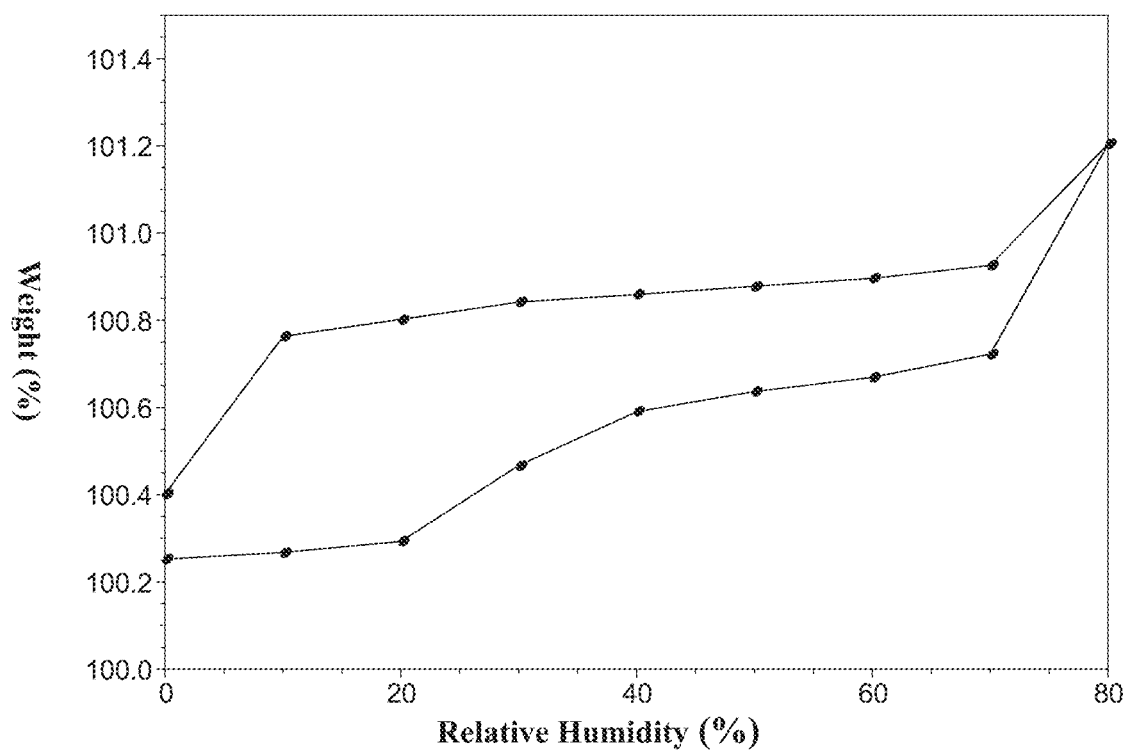
FIG. 21 is the isothermal sorption plot of LY2157299 Form 4 of the present invention.
Figure 22:
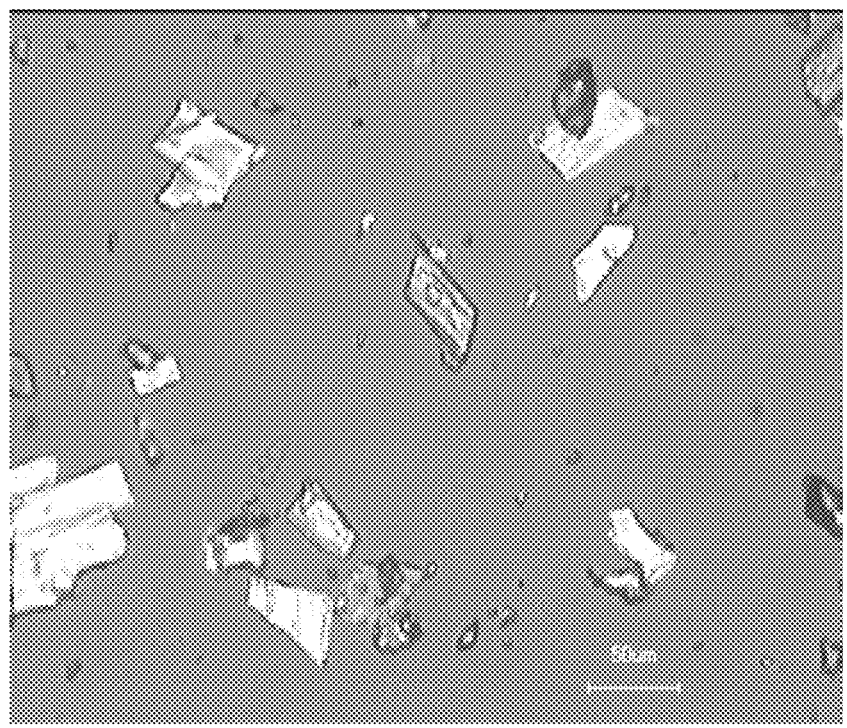
FIG. 22 is the PLM plot of LY2157299 Form 4 of the present invention.

Its XRPD plot is shown in FIG. 18.
Its DSC thermogram is shown in FIG. 19.
Its TGA thermogram is shown in FIG. 20.
Its isothermal sorption curve is shown in FIG. 21.
Its PLM plot is shown in FIG. 22.

Example 38

Took 25 mg of the LY2157299 Form 1 of Example 8, added 2 mL methanol to obtain a suspension, stirred at 60° C. for 3 days for crystallization, filtrated, then blast dried at room temperature for 1 hour to obtain 15 mg LY2157299 Form 4, 60% yield.

Example 39

Took 15 mg of the LY2157299 Form 1 of Example 8, added 0.3 mL methanol and 0.3 mL ethyl acetate to obtain a suspension, stirred at 4° C. for 7 days for crystallization, filtrated, then blast dried at room temperature for 1 hour to obtain 10 mg LY2157299 Form 4, 67% yield.

Example 40

Took 100 mg of the LY2157299 Form 1 of Example 8, added 1 mL ethanol and 1 mL ethyl acetate to obtain a suspension, stirred at 4° C. for 7 days, filtrated, then blast dried at room temperature for 1 hour to obtain 77 mg LY2157299 Form 4, 77% yield.

Example 41

Took 11 mg of the LY2157299 Form 1 of Example 8, added 0.5 mL ethanol and 0.6 mL n-heptane to obtain a suspension, stirred at 50° C. for 7 days, filtrated, then blast dried at room temperature for 1 hour to obtain 5 mg LY2157299 Form 4, 46% yield.

Example 42

Took 20 mg of the LY2157299 monohydrate of Preparation Example 1, at 50° C., added 1 mL methanol to obtain a solution, stirred at 5° C. for 0.5 hour for crystallization, filtrated, then vacuum dried at room temperature for 1 hour to obtain 13 mg LY2157299 Form 4, 68% yield.

Example 43

Took 18 mg of the LY2157299 monohydrate of Preparation Example 1, at 55° C., added 1.2 mL methanol and 0.6 mL MTBE to obtain a solution, stirred at 0° C. for 3 hours for crystallization, filtrated, then vacuum dried at room temperature for 1 hour to obtain 9 mg LY2157299 Form 4, 52% yield.

Example 44

Took 27 mg of the LY2157299 monohydrate of Preparation Example 1, at 55° C., added 0.6 mL methanol and 0.3 mL isopropyl acetate to obtain a solution, stirred at 0° C. for 3 hours for crystallization, filtrated, then vacuum dried at room temperature for 1 hour to obtain 16 mg LY2157299 Form 4, 62% yield.

Example 45

Took 30 mg of the LY2157299 monohydrate of Preparation Example 1, at 50° C., added 0.4 mL methanol and 0.2 mL isopropyl acetate to obtain a solution, naturally cooled to room temperature, then stirred at 5° C. for 2 hours for crystallization, filtrated, then vacuum dried at room temperature for 1 hour to obtain 15 mg LY2157299 Form 4, 52% yield.

Example 46

Took 20 mg of the LY2157299 monohydrate of Preparation Example 1, added 1 mL methanol to obtain a clear solution, added 2 mL pre-chilled diisopropyl ether, stirred at 5° C. for 0.5 hour for crystallization, filtrated, then vacuum dried at room temperature for 1 hour to obtain 10 mg LY2157299 Form 4, 52% yield.

Example 47

Took 30 mg of the LY2157299 monohydrate of Preparation Example 1, added 1 mL ethanol to obtain a clear solution, added 5 mL pre-chilled diisopropyl ether, stirred at 0° C. for 2 hours for crystallization, filtrated, then vacuum dried at room temperature for 1 hour to obtain 17 mg LY2157299 Form 4, 59% yield.

Example 48

Took 20 mg of the LY2157299 monohydrate of Preparation Example 1, added 4 mL n-butanol to obtain a clear solution, added 8 mL pre-chilled n-heptane, stirred at 0° C. for 2 hours for crystallization, filtrated, then vacuum dried at room temperature for 1 hour to obtain 10 mg LY2157299 Form 4, 52% yield.

XRPD patterns, DSC plots, PLM plots, isothermal sorption plots, TGA plots (not shown) of the samples prepared in Examples 38 to 48 are the same as or similar to that of the sample prepared in Example 37, indicating the crystalline forms obtained in Examples 38 to 48 are the same as that of Example 37.

Example 49

Took 50 mg of the LY2157299 monohydrate of Preparation Example 1, added 5 mL water-saturated trichloromethane to obtain a clear solution, evaporated open capped at 25° C. to dryness to obtain 40 mg LY2157299 Form 7, 82% yield.

Figure 25:
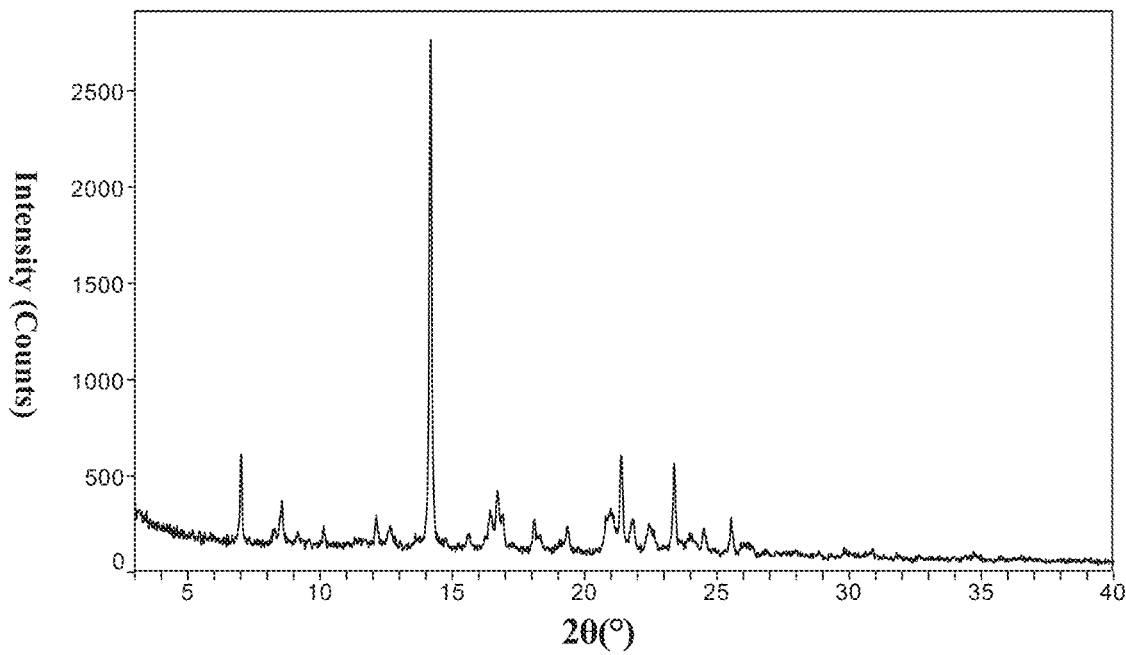
FIG. 25 is the XRPD plot of LY2157299 Form 7 of the present invention.
Figure 26:
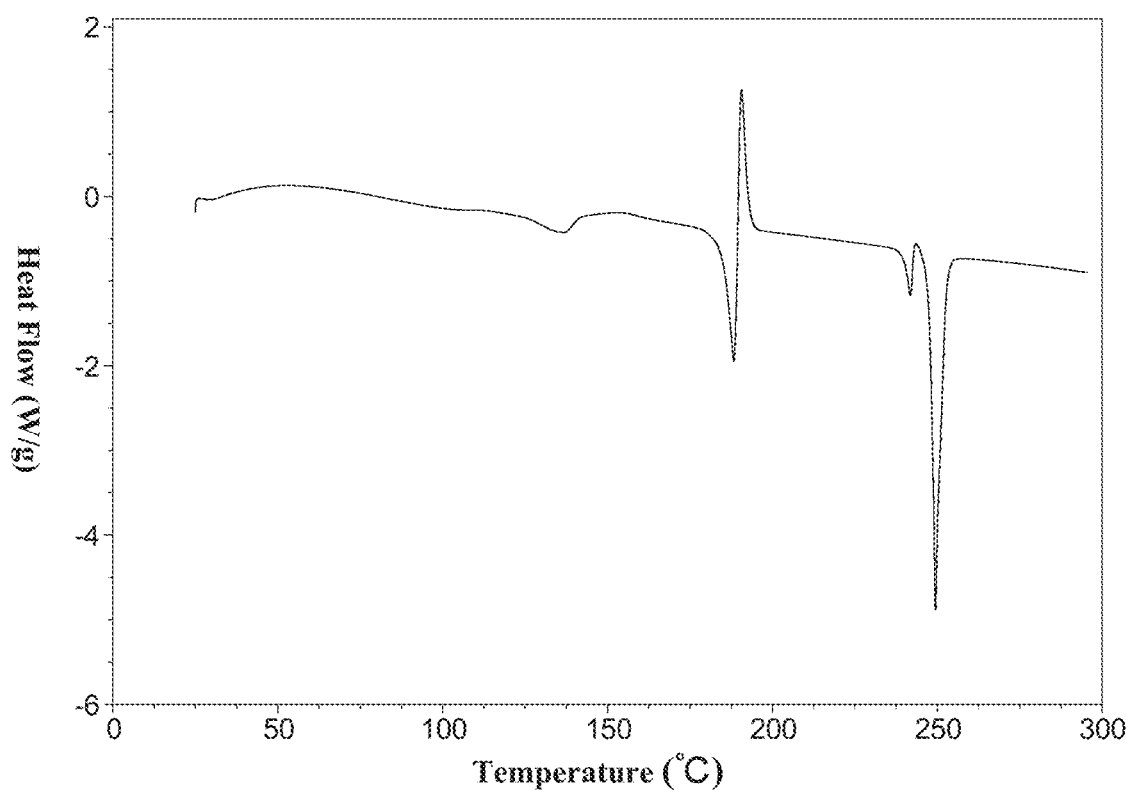
FIG. 26 is the DSC plot of LY2157299 Form 7 of the present invention.
Figure 27:
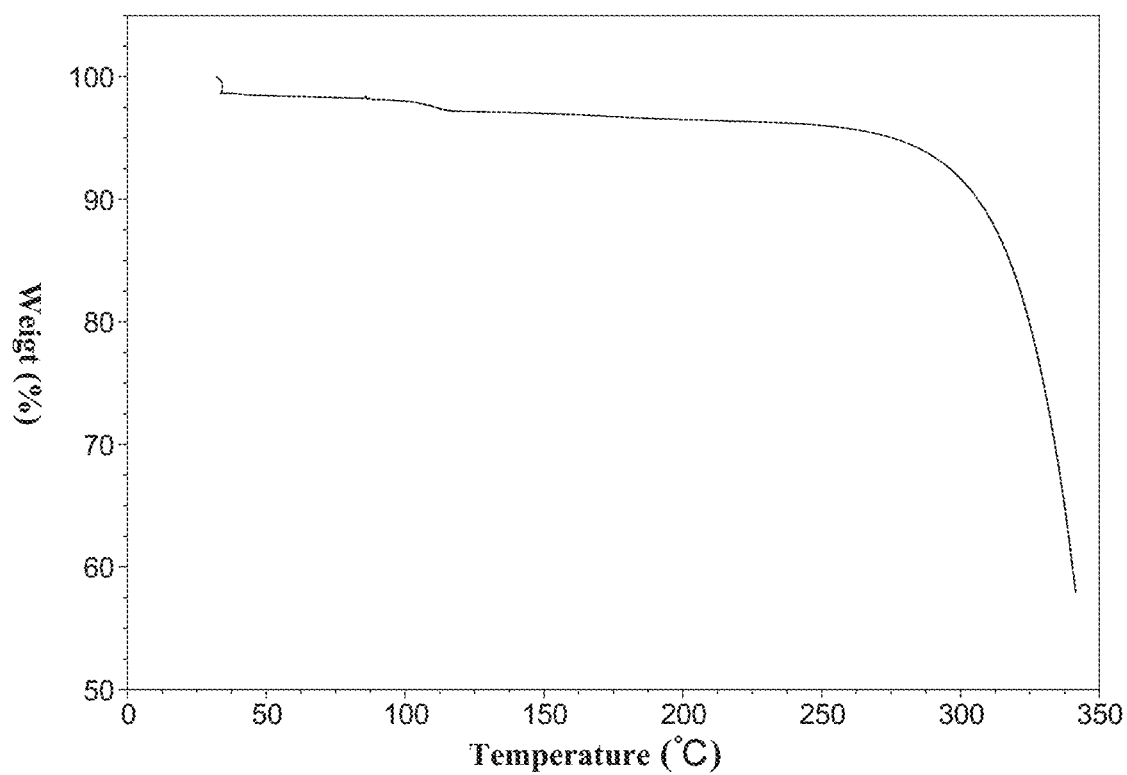
FIG. 27 is the TGA plot of LY2157299 Form 7 of the present invention.
Figure 28:
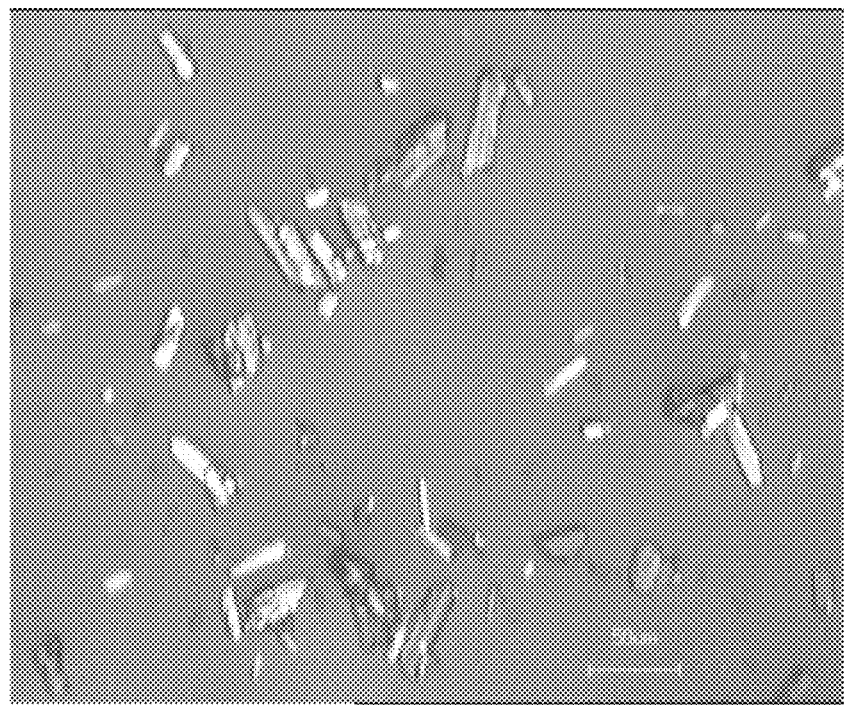
FIG. 28 is the PLM plot of LY2157299 Form 7 of the present invention.

Its XRPD plot is shown in FIG. 25.
Its DSC thermogram is shown in FIG. 26.
Its TGA thermogram is shown in FIG. 27.
Its PLM plot is shown in FIG. 28.

Example 50

Took 10 mg of the LY2157299 monohydrate of Preparation Example 1, added 0.8 mL water-saturated trichloromethane to obtain a clear solution, evaporated open capped at 30° C. to dryness to obtain 6 mg LY2157299 Form 7, 61% yield.

Example 51

Took 10 mg of the LY2157299 monohydrate of Preparation Example 1, added 0.4 mL water-saturated trichloromethane to obtain a clear solution, evaporated open capped at 40° C. to dryness to obtain 7 mg LY2157299 Form 7, 72% yield.

XRPD patterns, DSC plots, TGA plots, and PLM plots (not shown) of the samples prepared in Examples 50 to 51 are the same as or similar to that of the sample prepared in Example 49, indicating the crystalline forms obtained in Examples 50 to 51 are the same as that of Example 49.

Example 52

Took 40 mg of the LY2157299 monohydrate of Preparation Example 1, at 25° C., added 0.4 mL trifluoroethanol to obtain a clear solution, stirred at 0° C. for 0.5 hour for crystallization, filtrated, vacuum dried at room temperature for 1 hour to obtain 20 mg LY2157299 Form 5, 46% yield.

Figure 23:
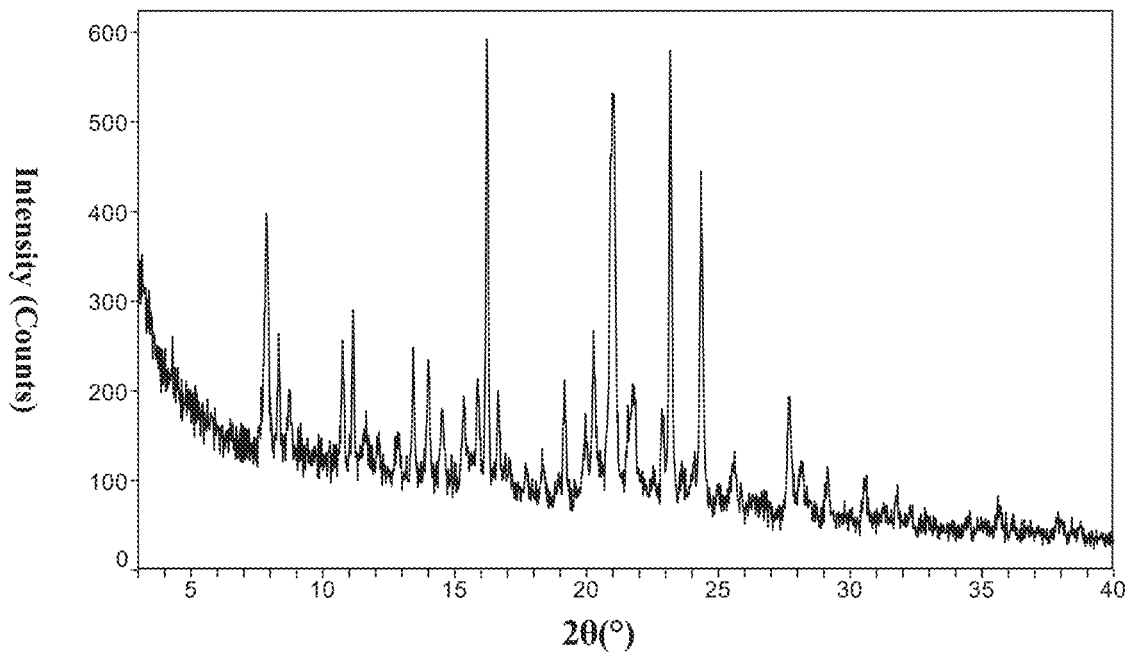
FIG. 23 is the XRPD plot of LY2157299 Form 5 of the present invention.

Its XRPD plot is shown in FIG. 23.

Example 53

Took 20 mg of the LY2157299 monohydrate of Preparation Example 1, at 50° C., added 0.2 mL trifluoroethanol and 0.2 mL diisopropyl ether to obtain a clear solution, stirred at 5° C. for 2 hours for crystallization, filtrated, vacuum dried at room temperature for 1 hour to obtain 10 mg LY2157299 Form 5, 46% yield.

Example 54

Took 20 mg of the LY2157299 monohydrate of Preparation Example 1, added 0.2 mL trifluoroethanol to obtain a clear solution, added 1 mL pre-chilled diisopropyl ether, stirred at 0° C. for 0.5 hour for crystallization, filtrated, vacuum dried at room temperature for 1 hour to obtain 12 mg LY2157299 Form 5, 55% yield.

Example 55

Took 30 mg of the LY2157299 monohydrate of Preparation Example 1, added 1 mL trifluoroethanol to obtain a clear solution, added 9 mL pre-chilled n-heptane, stirred at 5° C. for 2 hours for crystallization, filtrated, vacuum dried at room temperature for 1 hour to obtain 12 mg LY2157299 Form 5, 37% yield.

Example 56

Figure 24:
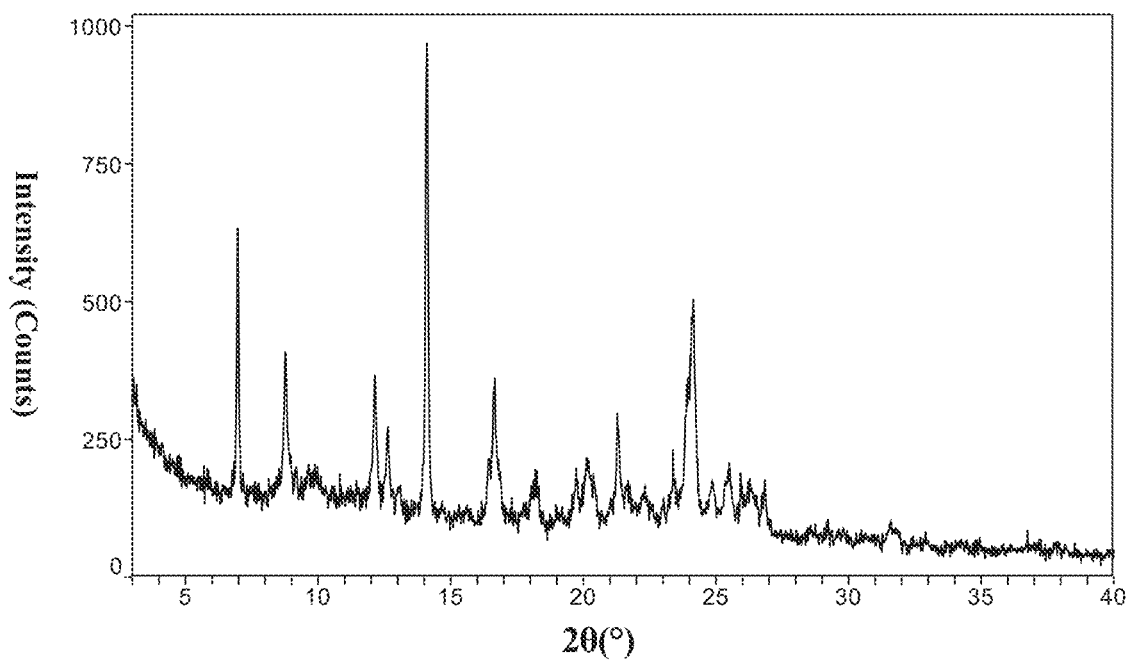
FIG. 24 is the XRPD plot of LY2157299 Form 6 of the present invention.

Took 10 mg of the LY2157299 monohydrate of Preparation Example 1, added 1 mL dichloromethane to obtain a clear solution, evaporated open-capped at 40° C. to dryness to obtain 6 mg LY2157299 Form 6, 60% yield.
Its XRPD plot is shown in FIG. 24.

Example 57

Took 10 mg of the LY2157299 monohydrate of Preparation Example 1, added 0.5 mL dichloromethane to obtain a clear solution, evaporated at reduced pressure at 30° C. to dryness to obtain 7 mg LY2157299 Form 6, 69% yield.

Example 58

Took 20 mg of the LY2157299 monohydrate of Preparation Example 1, added 0.8 mL dichloromethane to obtain a clear solution, added 1 mL pre-chilled n-heptane, stirred at 0° C. for 0.5 hour for crystallization, filtrated, vacuum dried at room temperature for 1 hour to obtain 12 mg LY2157299 Form 6, 60% yield.

Example 59

Took 20 mg of the LY2157299 monohydrate of Preparation Example 1, added 2 mL dichloromethane to obtain a clear solution, added 2 mL pre-chilled diisopropyl ether, stirred at 5° C. for 2 hours for crystallization, filtrated, vacuum dried at room temperature for 1 hour to obtain 10 mg LY2157299 Form 6, 50% yield.

Example 60

Figure 29:
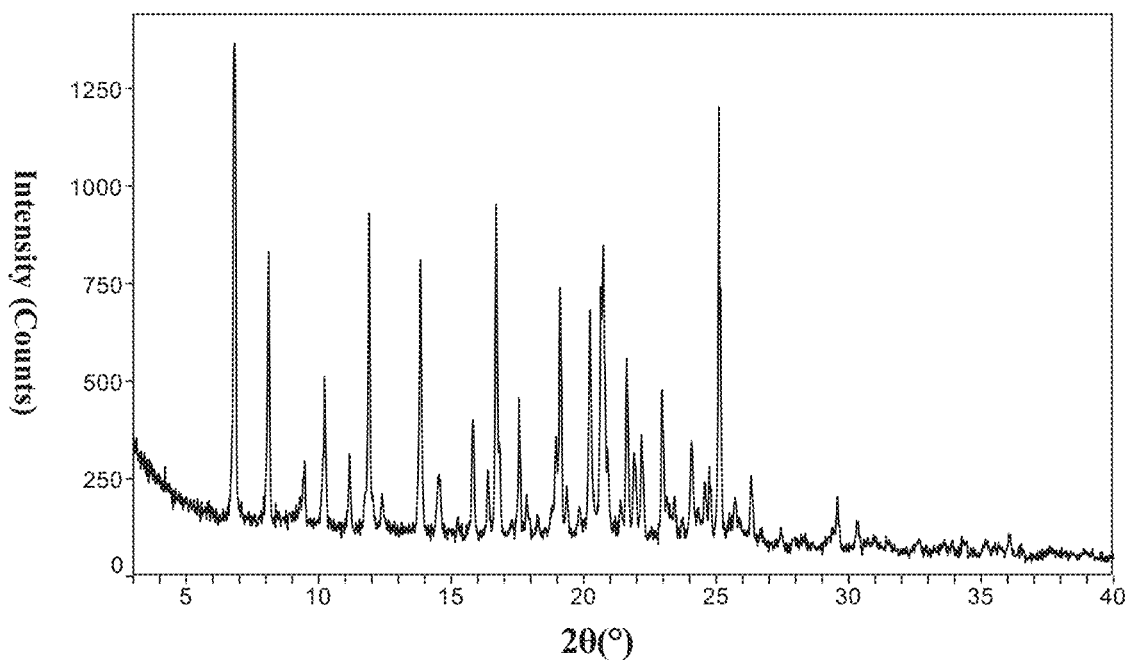
FIG. 29 is the XRPD plot of LY2157299 Form 8 of the present invention.

Took 10 mg of the LY2157299 monohydrate of Preparation Example 1, added 0.8 mL 2-butanol to obtain a clear solution, evaporated at 40° C. to dryness to obtain 7 mg LY2157299 Form 8, 70% yield.
Its XRPD plot is shown in FIG. 29.

Example 61

Figure 30:
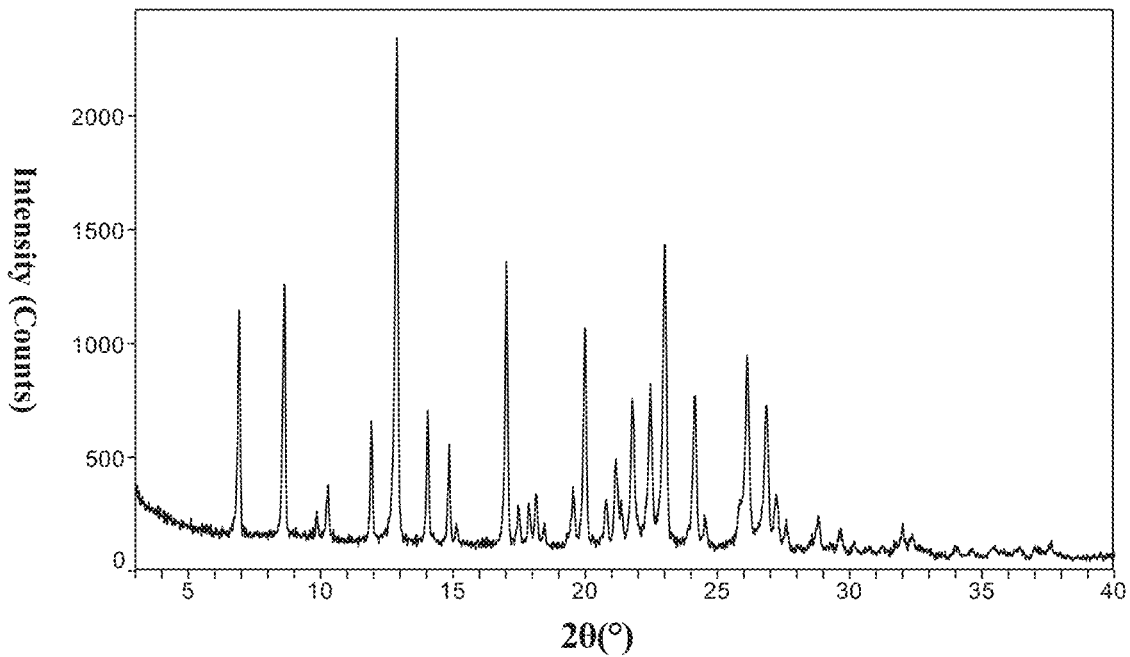
FIG. 30 is the XRPD plot of LY2157299 Form 9 of the present invention.

Took 100 mg of the LY2157299 monohydrate of Preparation Example 1, added 1 mL nitromethane to obtain a suspension, stirred at 25° C. for 7 days, filtrated, then vacuum dried at room temperature for 2 hours to obtain 75 mg LY2157299 Form 9, 75% yield.
Its XRPD plot is shown in FIG. 30.

Example 62

Took 30 mg of the LY2157299 monohydrate of Preparation Example 1, at 50° C., added 2 mL dichloromethane to obtain a clear solution, added 3 mL pre-chilled diisopropyl ether, stirred at 0° C. for 1 hour, filtrated, vacuum dried at room temperature for 1 hour to obtain 15 mg LY2157299 Form 9, 50% yield.

Example 63

Figure 31:
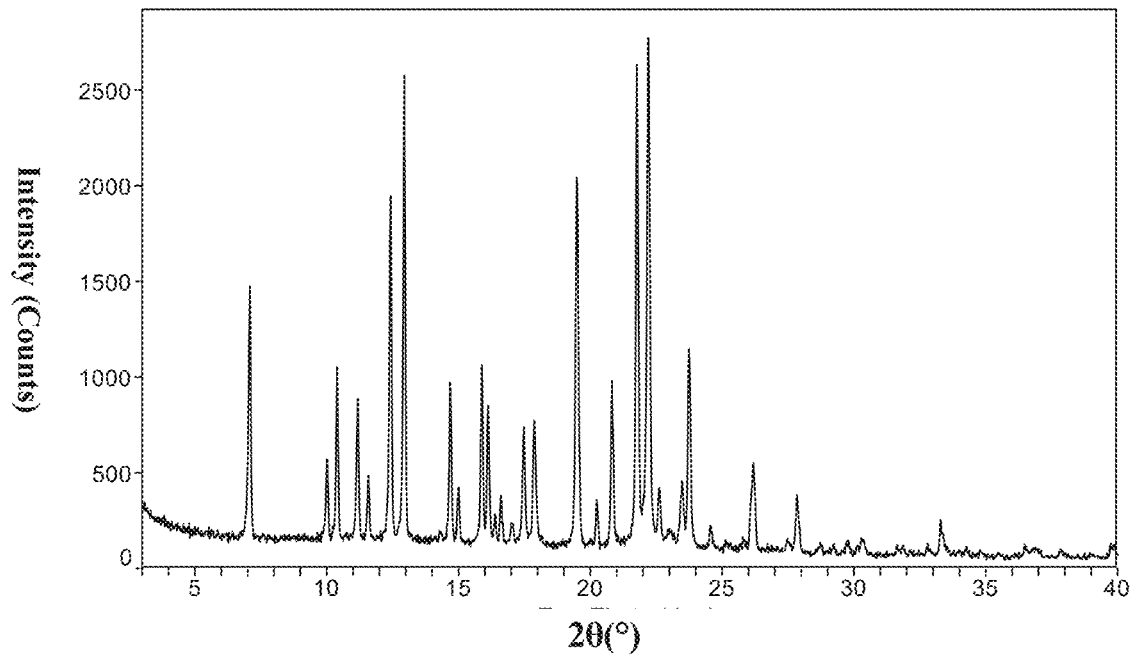
FIG. 31 is the XRPD plot of LY2157299 Form 10 of the present invention.

Took 20 mg of the LY2157299 monohydrate of Preparation Example 1, added 0.4 mL isopropanol to obtain a suspension, stirred at 25° C. for 5 days, filtrated, vacuum dried at room temperature for 1 hour to obtain 12 mg LY2157299 Form 10, 60% yield.
Its XRPD plot is shown in FIG. 31.

Example 64

Took 20 mg of the LY2157299 monohydrate of Preparation Example 1, at 50° C., added 2.5 mL isopropanol to obtain a solution, cooled at 10° C./hr to 0° C., filtrated, vacuum dried at room temperature for 1 hour to obtain 10 mg LY2157299 Form 10, 50% yield.

Example 65

Figure 32:
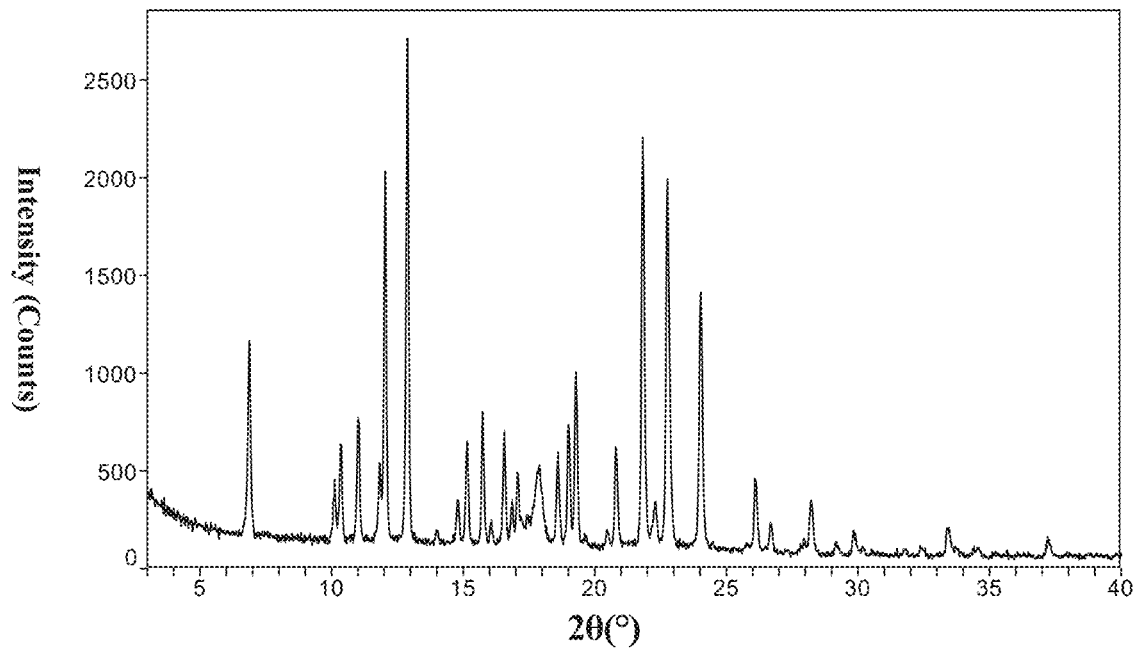
FIG. 32 is the XRPD plot of LY2157299 Form 11 of the present invention.

Took 20 mg of the LY2157299 monohydrate of Preparation Example 1, added 0.4 mL n-propanol to obtain a suspension, stirred at 25° C. for 5 days, filtrated, vacuum dried at room temperature for 1 hour to obtain 8 mg LY2157299 Form 11, 40% yield.
Its XRPD plot is shown in FIG. 32.

Example 66

Took 20 mg of the LY2157299 monohydrate of Preparation Example 1, at 50° C., added 0.4 mL n-propanol to obtain a solution, cooled at 10° C./hr to 0° C., filtrated, vacuum dried at room temperature for 1 hour to obtain 10 mg LY2157299 Form 11, 50% yield.

Example 67

Figure 33:
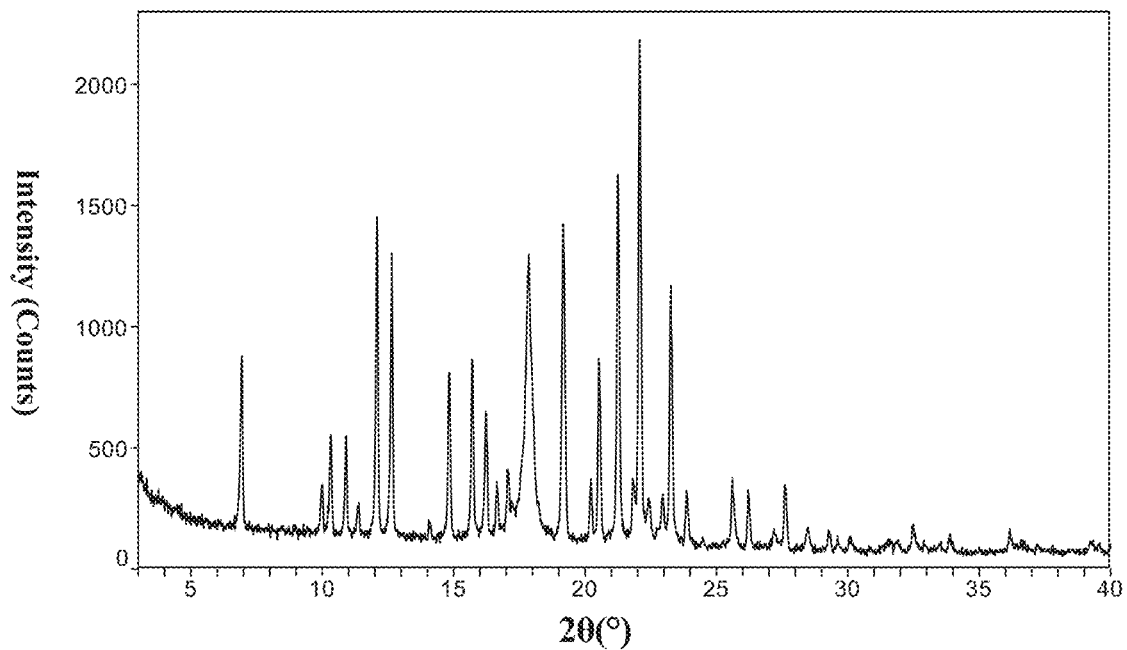
FIG. 33 is the XRPD plot of LY2157299 Form 12 of the present invention.

Took 15 mg of the LY2157299 monohydrate of Preparation Example 1, added 0.4 mL 2-butanol to obtain a suspension, stirred at 25° C. for 5 days, filtrated, vacuum dried at room temperature for 1 hour to obtain 8 mg LY2157299 Form 12, 53% yield.
Its XRPD plot is shown in FIG. 33.

Example 68

Figure 34:
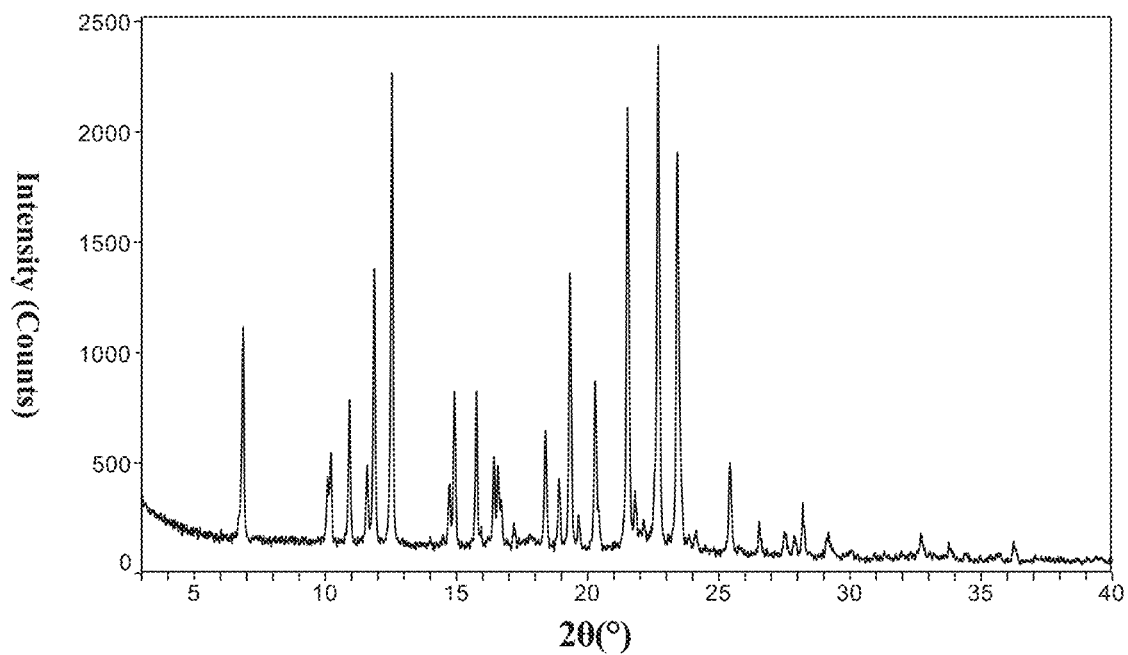
FIG. 34 is the XRPD plot of LY2157299 Form 13 of the present invention.

Took 20 mg of the LY2157299 monohydrate of Preparation Example 1, added 0.4 mL n-butanol to obtain a suspension, stirred at 25° C. for 5 days, filtrated, vacuum dried at room temperature for 1 hour to obtain 11 mg LY2157299 Form 13, 55% yield.
Its XRPD plot is shown in FIG. 34.

Example 69

Took 20 mg of the LY2157299 monohydrate of Preparation Example 1, at 50° C., added 0.8 mL n-butanol to obtain a solution, cooled at 10° C./hr to 5° C., filtrated, vacuum dried at room temperature for 1 hour to obtain 10 mg LY2157299 Form 13, 50% yield.

Example 70

Took 20 mg of the LY2157299 monohydrate of Preparation Example 1, at 50° C., added 1 mL n-butanol to obtain a clear solution, added 2 mL pre-chilled n-heptane, stirred at 0° C. for 1 hour, filtrated, vacuum dried at room temperature for 1 hour to obtain 11 mg LY2157299 Form 13, 55% yield.

Example 71

Took 15 mg of the LY2157299 monohydrate of Preparation Example 1, added 0.6 mL toluene to obtain a suspension, stirred at 25° C. for 5 days, filtrated, vacuum dried at room temperature for 1 hour to obtain 7 mg LY2157299 Form 14, 47% yield.

Figure 35:
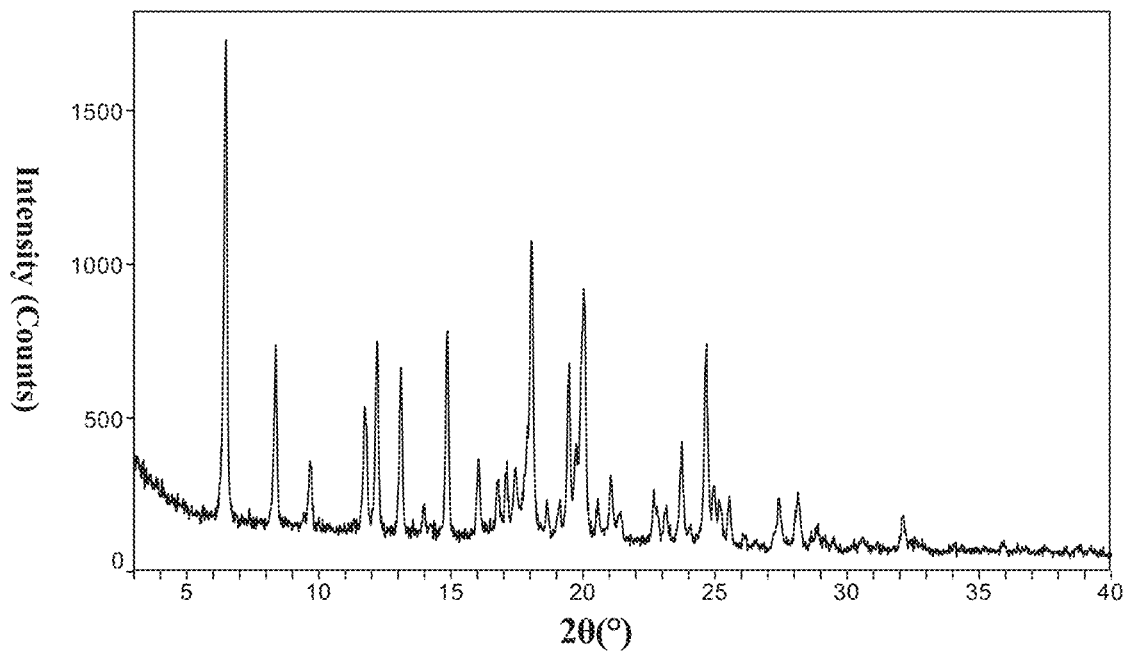
FIG. 35 is the XRPD plot of LY2157299 Form 14 of the present invention.

Its XRPD plot is shown in FIG. 35.

Example 72

Took 20 mg of the LY2157299 monohydrate of Preparation Example 1, added 0.4 mL ethanol to obtain a suspension, stirred at room temperature for 5 days, filtrated, vacuum dried at room temperature for 1 hour to obtain 11 mg LY2157299 Form 15, 55% yield.

Figure 36:
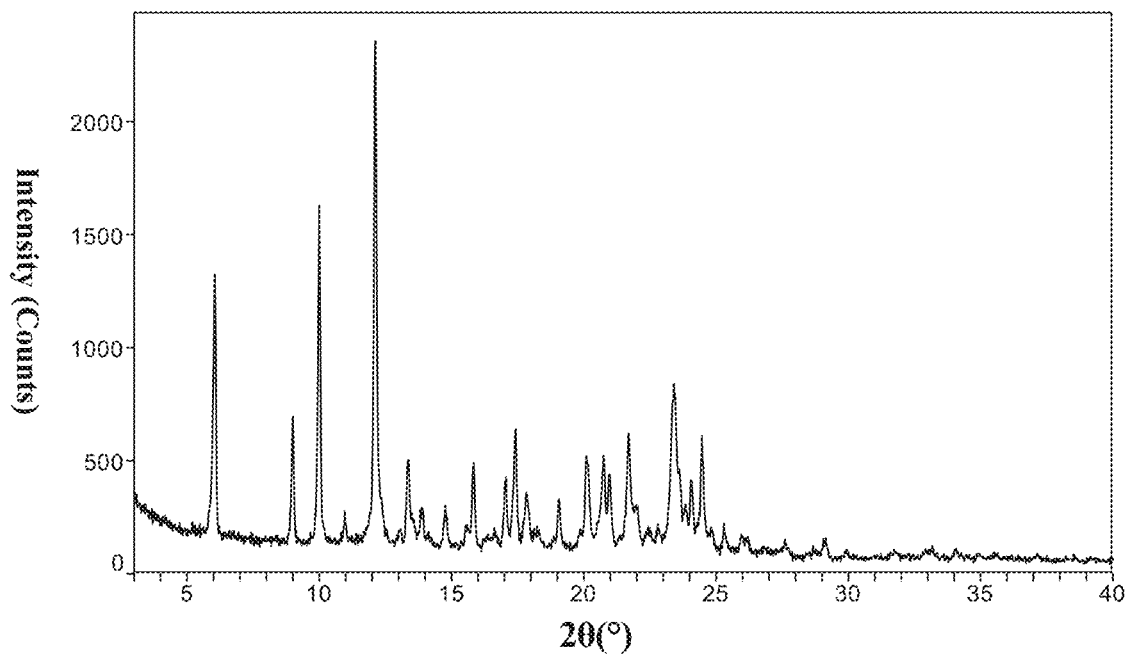
FIG. 36 is the XRPD plot of LY2157299 Form 15 of the present invention.

Its XRPD plot is shown in FIG. 36.

Example 73

Took 20 mg of the LY2157299 monohydrate of Preparation Example 1, at 55° C., added 1 mL ethanol to obtain a solution, cooled at 10° C./hr to 5° C., filtrated, vacuum dried at room temperature for 1 hour to obtain 10 mg LY2157299 Form 15, 50% yield.

Example 74

Took 20 mg of the LY2157299 monohydrate of Preparation Example 1, at 50° C., added 1 mL acetone to obtain a solution, cooled at 10° C./hr to 5° C., filtrated, vacuum dried at room temperature for 1 hour to obtain 12 mg LY2157299 Form 16, 60% yield.

Figure 37:
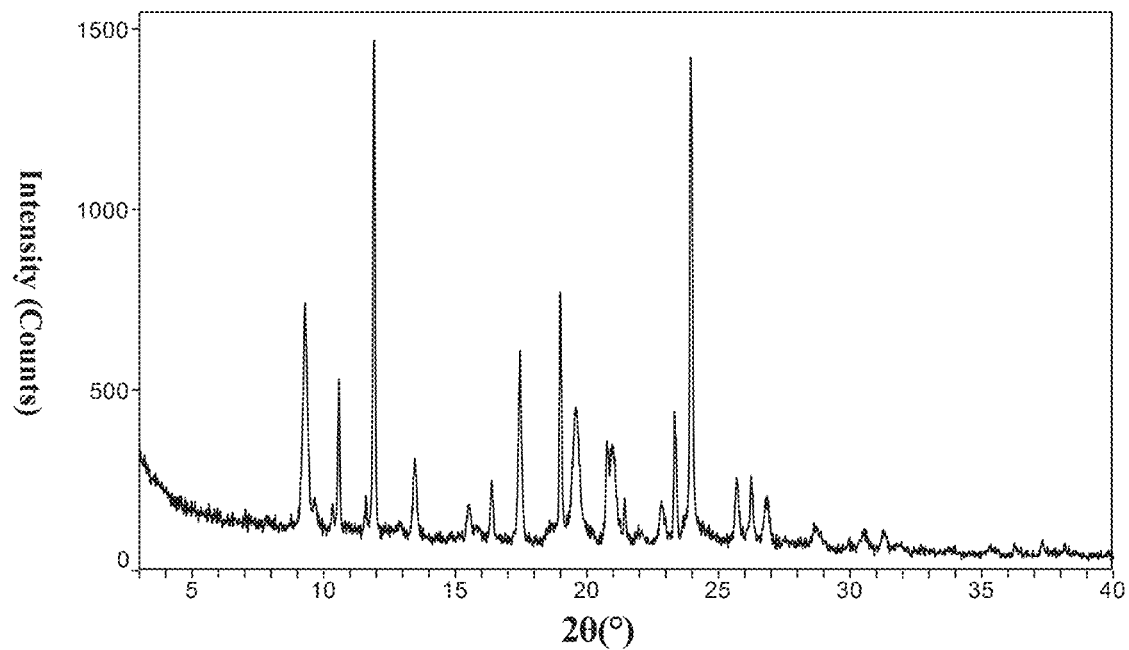
FIG. 37 is the XRPD plot of LY2157299 Form 16 of the present invention.

Its XRPD plot is shown in FIG. 37.

Example 75

Took 20 mg of the LY2157299 monohydrate of Preparation Example 1, at 50° C., added 1 mL butanone to obtain a solution, cooled at 10° C./hr to 5° C., filtrated, vacuum dried at room temperature for 1 hour to obtain 10 mg LY2157299 Form 17, 50% yield.

Figure 38:
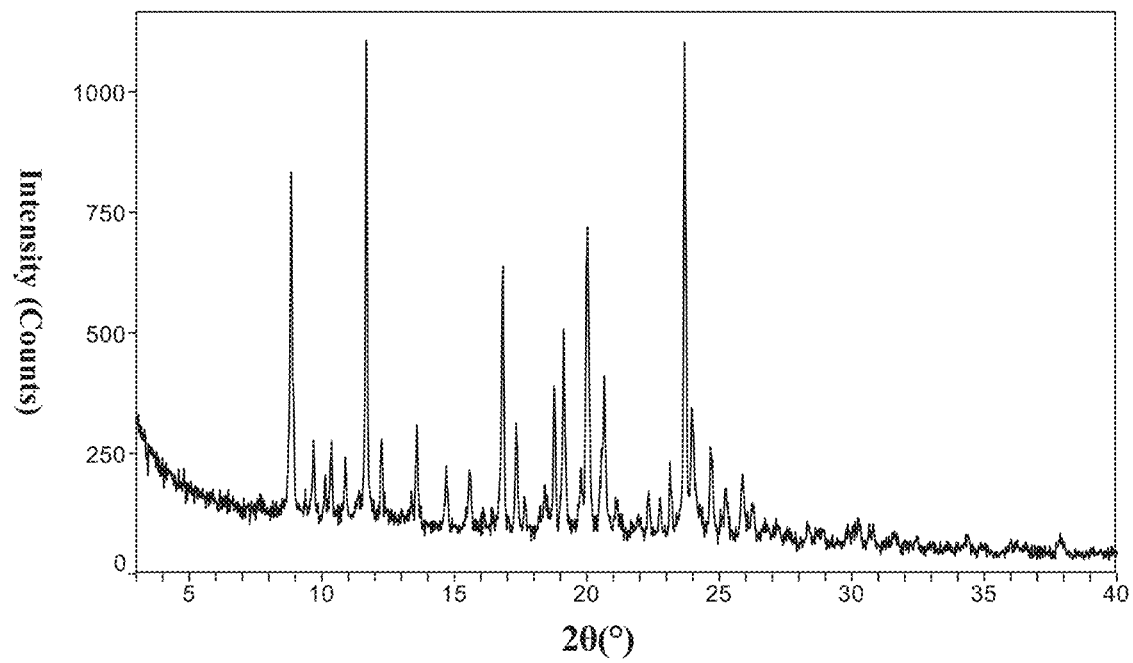
FIG. 38 is the XRPD plot of LY2157299 Form 17 of the present invention.

Its XRPD plot is shown in FIG. 38.

Example 76

Took 20 mg of the LY2157299 monohydrate of Preparation Example 1, at 55° C., added 4 mL ethyl acetate to obtain a solution, cooled at 10° C./hr to 5° C., filtrated, vacuum dried at room temperature for 1 hour to obtain 9 mg LY2157299 Form 18, 45% yield.

Figure 39:
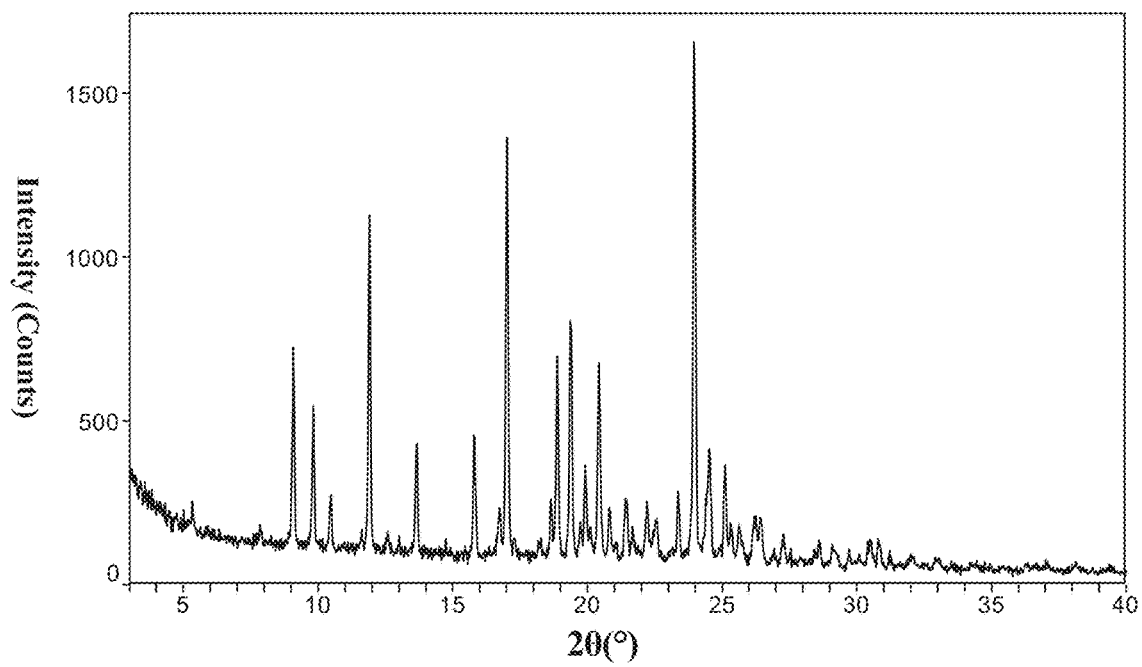
FIG. 39 is the XRPD plot of LY2157299 Form 18 of the present invention.

Its XRPD plot is shown in FIG. 39.

Example 77

Took 20 mg of the LY2157299 monohydrate of Preparation Example 1, added 0.4 mL 1,4-dioxane to obtain a suspension, stirred at room temperature for 5 days, filtrated, vacuum dried at room temperature for 1 hour to obtain 11 mg LY2157299 Form 19, 55% yield.

Figure 40:
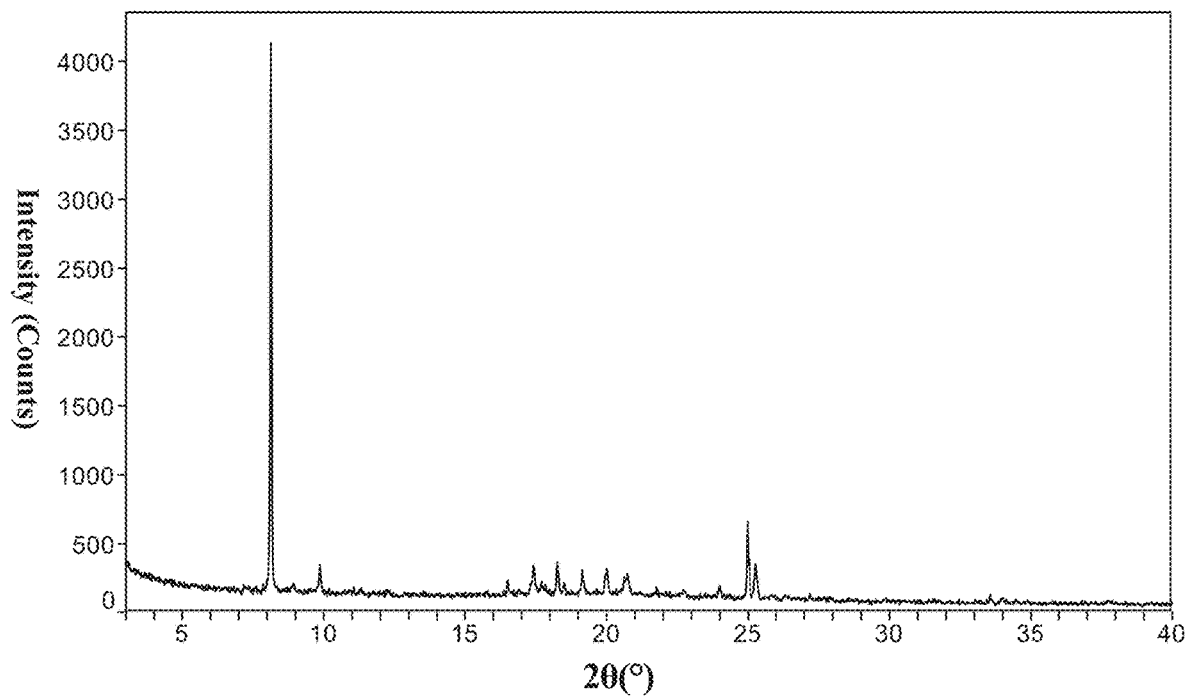
FIG. 40 is the XRPD plot of LY2157299 Form 19 of the present invention.

Its XRPD plot is shown in FIG. 40.

Example 78

Took 10 mg of the LY2157299 monohydrate of Preparation Example 1, added 0.8 mL 1,4-dioxane to obtain a solution, evaporated at reduced pressure at 30° C. to dryness to obtain 7 mg LY2157299 Form 19, 70% yield.

Example 79

Took 20 mg of the LY2157299 monohydrate of Preparation Example 1, at 50° C., added 1 mL 1,4-dioxane to obtain a solution, added 2 mL pre-chilled n-heptane, stirred at 0° C. for 1 hour, filtrated, vacuum dried at room temperature for 1 hour to obtain 11 mg LY2157299 Form 19, 55% yield.

Example 80

Took 10 mg of the LY2157299 monohydrate of Preparation Example 1, added 2 mL acetonitrile to obtain a clear solution, evaporated at reduced pressure at 30° C. to dryness to obtain 6 mg amorphous LY2157299, 60% yield.

Figure 41:
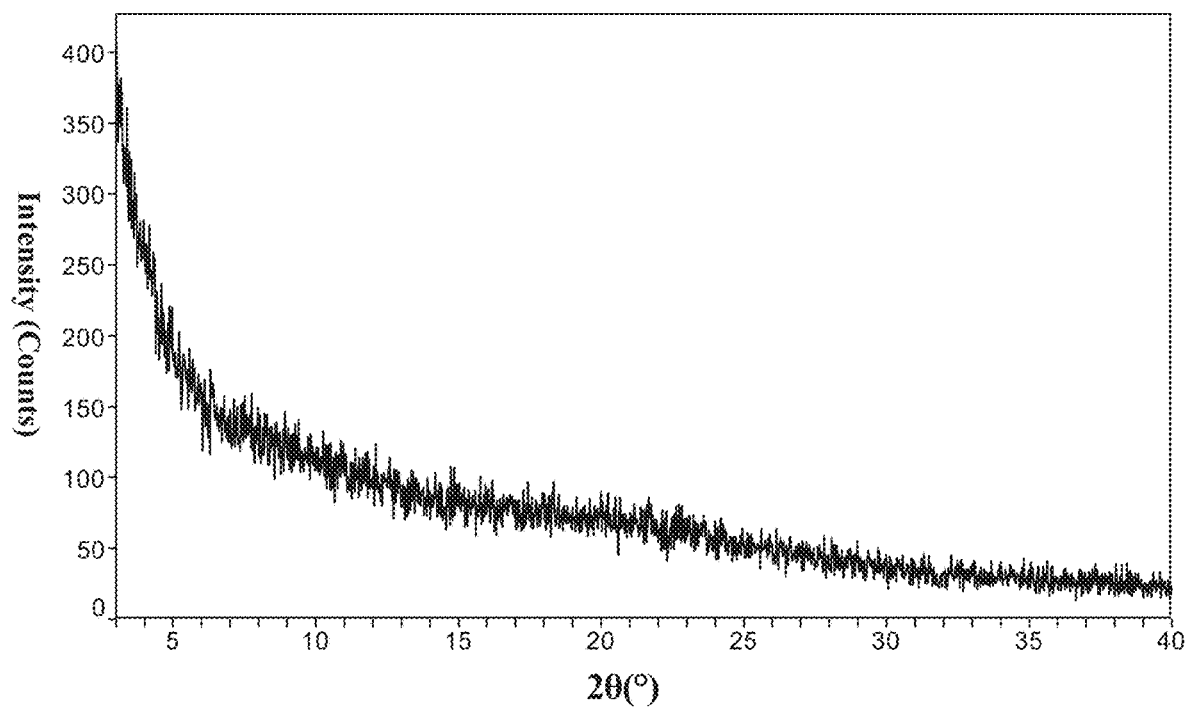
FIG. 41 is the XRPD plot of the amorphous LY2157299 of the present invention.

Its XRPD plot is shown in FIG. 41.

Example 81

| Component | Amount (mg) |
| --- | --- |
| LY2157299 Form 1 or Form 2 or Form 3 or Form 4 or Form 7 (active ingredient basis) | 80 |
| Microcrystalline cellulose | 310 |
| silicon dioxide | 5 |
| Talc | 5 |
| Total | 400 |

Mixed LY2157299Form 1 or Form 2 or Form 3 or Form 4 or Form 7, starch, microscystalline cellulose, silicon dioxide, and talc and then filled to capsules.

Example 82

| Component | Amount(mg) |
| --- | --- |
| LY2157299 Form 1 or Form 2 or Form 3 or Form 4 or Form 7 (active ingredient basis) | 150 |
| Microcrystalline cellulose | 50 |
| Starch | 59 |
| Hydroxypropyl methylcellulose (5% water solution) | 5.0 |
| Carboxymethyl starch sodium | 4.5 |
| Magnesium stearate | 1.0 |
| Talc | 1.5 |
| Total | 270 |

Sieved LY2157299 Form 1 or Form 2 or Form 3 or Form 4 or Form 7, starch, and microcrystalline cellulose to a #20 sieve, and thoroughly mixed them. Mixed hydroxypropyl methylcellulose solution with the mixed powders, then pass it to a #16 sieve, dried the granules then passed a #16 sieve. Passed carboxymethyl starch sodium, magnesium stearate and talc to a #30 sieve, added them to the above granules, mixed and pressed into tablets using tablet press, each tablet weighed 270 mg.

Comparative Example 1

Performed water solubility test on LY2157299 monohydrate of Preparation Example 1 and LY2157299 Form 1, Form 2, Form 3, Form 4, and Form 7, the details are below:

Accurately weighed 5 mg samples in a 200 mL flask which was in a water bath with temperature 25° C.±2° C., added water in a geometric fashion the flask, stirred (about 200 r/min), and observed by naked eyes to see if it was clear. Water was added every 3 mins, maximum water amount 100 mL.

The results are shown in the following table. It shows LY2157299 Form 1, Form 2, Form 3, Form 4, and Form 7 all had better water solubility than the known LY2157299 monohydrate.

| Form | Solubility (μg/mL) |
|---|---|
| LY2157299 Monohydrate | <50 |
| LY2157299 Form 1 | 160 |
| LY2157299 Form 2 | 200 |
| LY2157299 Form 3 | 150 |
| LY2157299 Form 4 | 100 |
| LY2157299 Form 7 | 100 |

The described above are only specific embodiments for illustrating the present invention, but without limiting it to that. Any changes or alternations, without creative work, made by those skilled in the art within the technical scope disclosed by the present invention, should fall within the scope of the present invention. Therefore, the scope of protection of the present invention shall be subject to the scope of protection defined in the claims.

What is claimed is:

1. Crystalline Form 1 of galunisertib of formula (I):

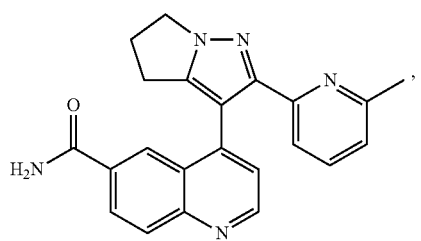

(I)

wherein the crystalline Form 1 is characterized by a powder X-ray diffraction pattern comprising diffraction peaks at angles (° 2θ) of 10.2°±0.2°, 14.6°±0.2°, 15.8°±0.2°, 19.0°±0.2°, 19.4°±0.2°, and 21.9°±0.2°.

2. The crystalline Form 1 according to claim 1, wherein the crystalline Form 1 is further characterized by a powder X-ray diffraction pattern comprising additional diffraction peaks at angles (° 2θ) of 11.2°±0.2°, 12.4°±0.2°, 16.8°±0.2°, 19.8°±0.2°, 23.2°±0.2°, and 25.1°±0.2°.

3. The crystalline Form 1 according to claim 1, wherein the crystalline Form 1 is further characterized by a powder X-ray diffraction pattern as shown in FIG. 6.

4. A pharmaceutical composition comprising at least one pharmaceutically acceptable carrier or additive and a therapeutically effective amount of the crystalline Form 1 according to claim 1.

5. The pharmaceutical composition according to claim 4, wherein the pharmaceutical composition is a dosage form selected from the group consisting of an aerosol, a capsule, a cream, an injectable solution, an ointment, a powder, a suppository, a suspension, a syrup, and a tablet.

6. A method for treating a disease in a subject, wherein the method comprises administering to the subject in need thereof a therapeutically effective amount of the crystalline Form 1 according to claim 1;
wherein the disease is caused by abnormal transforming growth factor beta activity in the subject; and
wherein the disease is selected from the group consisting of a cancer, a pre-cancer, a kidney disease, fibrosis, and an eye disease.

7. A method for treating a disease in a subject, wherein the method comprises administering to the subject in need thereof the pharmaceutical composition according to claim 4;
wherein the disease is caused by abnormal transforming growth factor beta activity in the subject; and
wherein the disease is selected from the group consisting of a cancer, a pre-cancer, a kidney disease, fibrosis, and an eye disease.

8. The method according to claim 7, wherein the pharmaceutical composition comprises 0.5 mg to 500 mg of the crystalline Form 1 according to claim 1.

9. The method according to claim 8, wherein the pharmaceutical composition comprises 150 mg of the crystalline Form 1 according to claim 1.

10. The method according to claim 8, wherein the pharmaceutical composition comprises 20 mg of the crystalline Form 1 according to claim 1.

11. The method according to claim 7, wherein the disease is a cancer.

12. The method according to claim 7, wherein the disease is a pre-cancer.

13. The method according to claim 7, wherein the disease is a kidney disease.

14. The method according to claim 7, wherein the disease is fibrosis.

15. The method according to claim 7, wherein the disease is an eye disease.

16. The method according to claim 7, wherein the subject is a human.

17. A process for preparing the crystalline Form 1 according to claim 1, wherein the process comprises the following steps:
(1) forming a solution of galunisertib dissolved in a co-solvent selected from the group consisting of acetone and methyl ethyl ketone, or a mixture thereof;
(2) adding the solution provided in step (1) dropwise to an anti-solvent selected from the group consisting of n-heptane, methyl tert-butyl ether, diethyl ether, and diisopropyl ether, or a mixture thereof, to provide a suspension;
(3) stirring the suspension provided in step (2) at a temperature in the range of 0° C. to 5° C. for a period of 0.5 hour to 2 hours, to afford a precipitate;
(4) crystallizing the precipitate provided in step (3); and
(5) drying the crystal provided in step (4) to obtain the crystalline Form 1 according to claim 1.

18. The process according to claim 17, wherein the mass to volume ratio of galunisertib to the co-solvent is in the range of 5 mg:1 mL to 40 mg:1 mL.

19. A process for preparing the crystalline Form 1 according to claim 1, wherein the process comprises the following steps:
(1) heating galunisertib monohydrate to a temperature in the range of 130° C. to 180° C. at a rate in the range of 1° C./minute to 50° C./minute; and
(2) cooling to room temperature at a rate in the range of 1° C./minute to 50° C./minute, to obtain the crystalline Form 1 according to claim 1.

20. The process according to claim 19, wherein the heating galunisertib monohydrate to a temperature in the range of 130° C. to 180° C. in step (1) is performed at a rate in the range of 1° C./minute to 10° C./minute.

\* \* \* \* \*